US012331289B2

(12) United States Patent
Chaput

(10) Patent No.: US 12,331,289 B2
(45) Date of Patent: Jun. 17, 2025

(54) SCREENING ARTIFICIAL NUCLEIC ACIDS BY PARTICLE DISPLAY

(71) Applicant: THE REGENTS OF THE UNIVERSITY OF CALIFORNIA, Oakland, CA (US)

(72) Inventor: John Chaput, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/168,066

(22) Filed: Feb. 13, 2023

(65) Prior Publication Data
US 2023/0193253 A1 Jun. 22, 2023

Related U.S. Application Data

(63) Continuation of application No. 16/864,703, filed on May 1, 2020, now Pat. No. 11,591,593.

(60) Provisional application No. 62/842,022, filed on May 2, 2019.

(51) Int. Cl.
*C12N 15/115* (2010.01)
*C12N 15/10* (2006.01)
*C12Q 1/68* (2018.01)

(52) U.S. Cl.
CPC ........ *C12N 15/1093* (2013.01); *C12N 15/115* (2013.01); *C12N 2310/16* (2013.01)

(58) Field of Classification Search
None
See application file for complete search history.

(56) References Cited

U.S. PATENT DOCUMENTS

2009/0131352 A1  5/2009  Dahma
2016/0145606 A1  5/2016  Chaput

FOREIGN PATENT DOCUMENTS

WO  2014107502  7/2014

OTHER PUBLICATIONS

Alves Ferreira-Bravo, 2015, "Selection of 2'-deoxy-2'-fluoroarabinonucleotide (FANA) aptamers that bind HIV-1 reverse transcriptase with picomolar affinity," Nucleic Acids Res. 43:9587-9599.
Baker et al., 2015, "Reproducibility crisis: Blame it on the antibodies," Nature 521:274-276.
Bala et al., 2018, "Aptamers in HIV research diagnosis and therapy," RNA Biol 15:327-337.
Begley and Ellis, 2012, "Raise standards for preclinical cancer research," Nature 483:531-533.
Bowman et al., 2001, "Evaluation of phosphodiesterase I-based protocols for the detection of multiply damaged sites in DNA: the detection of abasic, oxidative and alkylative tandem damage in DNA oligonucleotides," Nucleic Acids Res. 29:E101.
Bradbury and Pluckthun, 2015, "Reproducibility: Standardize antibodies used in research," Nature, 518:27-29.
Chaput et al., 2012, "The emerging world of synthetic genetics," Chem. Biol. 19, 1360-1371.
Chim et al., 2017, "Structural basis for TNA synthesis by an engineered TNA polymerase", Nat Commun 8, 1810, 11 pages.
Cho et al., 2009, "Applications of aptamers as sensors," Annu Rev Anal Chem 2:241-264.
Culbertson et al., 2016, "Evaluating TNA stability under simulated physiological conditions," Bioorg. Med. Chem. Lett. 26:2418-2421.
Diafa, S et al., 2015, "Generation of Aptamers with an Expanded Chemical Repertoire. Molecules," 20:16643-16671.
Dunn and Chaput, 2016, "Reverse Transcription of Threose Nucleic Acid by a Naturally Occurring DNA Polymerase," ChemBioChem 17:1804-1808.
Dunn et al., 2014, "An In Vitro Selection Protocol for Threose Nucleic Acid (TNA) Using DNA Display," Current Protocols in Nucleic Acid Chemistry 9.8.1-9.8.19.
Eaton et al., 1997, "Post-SELEX combinatorial optimization of aptamers," Bioorg. Med. Chem. 5:1087-1096.
Egelhofer et al., 2011, "An assessment of histone-modification antibody quality," Nat. Struct. Mol. Biol. 18, 91-93.
Ellington and Szostak, 1990, "In vitro selection of RNA molecules that bind specific ligands," Nature 346:818-822.
Eremeeva, E et al., 2019, "Highly stable hexitol based XNA aptamers targeting the vascular endothelial growth factor," Nucleic Acids Research. 47:4927-4939.
Eschenmoser, 1999, "Chemical etiology of nucleic acid structure," Science, 284:2118-2124.
Gold et al., 2010, "Aptamer-Based Multiplexed Proteomic Technology for Biomarker Discovery," Plos One, 5: e15004.
Ichida et al., 2005, "An in Vitro Selection System for Tna," J. Am. Chem. Soc. 127:2802-2803.
Keefe et al., 2010, "Aptamers as therapeutics," Nat. Rev. Drug Discov. 9:537-550.
Kimoto et al., 2013, "Generation of high-affinity DNA aptamers using an expanded genetic alphabet," Nat. Biotechnol. 31:453-457.
Larsen et al., 2016, "A general strategy for expanding polymerase function by droplet microfluidics," Nat. Commun. 7:11235.
Marx et al., 2013, "Calling the next generation of affinity reagents," Nat. Methods 10:829-833.
Mei et al., 2018, "Synthesis and Evolution of a Threose Nucleic Acid Aptamer Bearing 7-Deaza-7-Substituted Guanosine Residues," J. Am. Chem. Soc. 140:5706-5713.
Michalowski et al., 2008, "Novel bimodular DNA aptamers with guanosine quadruplexes inhibit phylogenetically diverse HIV-1 reverse transcriptases," Nucleic Acids Res. 36:7124-7135.

(Continued)

*Primary Examiner* — Sean McGarry
(74) *Attorney, Agent, or Firm* — Riverside Law LLP

(57) ABSTRACT

The invention provides xeno-nucleic acid particle display libraries, methods for identifying functional non-natural nucleic acid (XNA) aptamers using the particle display libraries, and compositions comprising XNA aptamers identified by screening candidate molecules using the xeno-nucleic acid particle display libraries.

5 Claims, 6 Drawing Sheets

Specification includes a Sequence Listing.

(56) References Cited

OTHER PUBLICATIONS

Pinheiro, 2012, "Synthetic genetic polymers capable of heredity and evolution," Science, Apr. 20;336(6079):341-4.
Roberts and Szostak, 1997, "RNA-peptide fusions for the in vitro selection of peptides and proteins," Proc. Natl. Acad. Sci. USA 94:12297-12302.
Sau and Chaput, 2017, "A Gram-Scale HPLC-Free Synthesis of TNA Triphosphates Using an Iterative Phosphorylation Strategy", Org. Lett. 19, 4379-4382.
Sau et al., 2016, "A Scalable Synthesis of a-l-Threose Nucleic Acid Monomers," J. Org. Chem. 81:2302-2307.
Schoning et al., 2000, "Chemical etiology of nucleic acid structure: the a-threofuranosyl-(3'-->2') oligonucleotide system.", Science, 290, 1347-1351.
Vater and Klussmann, 2015, "Turning mirror-image oligonucleotides into drugs: the evolution of Spiegelmer® therapeutics," Drug Discov Today, 20:47-155.
Watts et al., 2009, "Studies on the hydrolytic stability of 2'-fluoroarabinonucleic acid (2'F-ANA)," Org Biomol Chem 7:1904-1910.
Wilson and Szoztak, 1999, "In vitro selection of functional nucleic acids," Ann. Rev. Biochem. 68:611-647.
Yang et al., 2007, "Experimental Evidence That GNA and TNA Were Not Sequential Polymers in the Prebiotic Evolution of Rna," J. Mol. Evol. 65:289-295.
Zhou and Rossi, 2017, "Aptamers as targeted therapeutics: current potential and challenges," Nat. Rev. Drug Discov. 16:181-202.
Zuker, 2003, "Mfold web server for nucleic acid folding and hybridization prediction," Nucleic Acids Res. 31:3406-3415.

SEQUENCE LISTING

```
Sequence total quantity: 17
SEQ ID NO: 1            moltype = DNA  length = 40
FEATURE                 Location/Qualifiers
misc_feature            1..40
                        note = Chemically synthesized
source                  1..40
                        mol_type = other DNA
                        organism = synthetic construct
SEQUENCE: 1
atagcaaatt acttataaat tagttcagta gctactgtca                          40

SEQ ID NO: 2            moltype = DNA  length = 40
FEATURE                 Location/Qualifiers
misc_feature            1..40
                        note = Chemically synthesized
source                  1..40
                        mol_type = other DNA
                        organism = synthetic construct
SEQUENCE: 2
agcaaagtcc ttggaatacg atcgtaccgt tcctagacta                          40

SEQ ID NO: 3            moltype = DNA  length = 40
```

```
FEATURE                 Location/Qualifiers
misc_feature            1..40
                        note = Chemically synthesized
source                  1..40
                        mol_type = other DNA
                        organism = synthetic construct
SEQUENCE: 3
aatagtaaat tgatttaaaa atttcataaa tgctacataa                              40

SEQ ID NO: 4            moltype = DNA  length = 38
FEATURE                 Location/Qualifiers
misc_feature            1..38
                        note = Chemically synthesized
source                  1..38
                        mol_type = other DNA
                        organism = synthetic construct
SEQUENCE: 4
tagtaaattg atttaaaaat ttcataaatg ctacataa                                38

SEQ ID NO: 5            moltype = DNA  length = 35
FEATURE                 Location/Qualifiers
misc_feature            1..35
                        note = Chemically synthesized
source                  1..35
                        mol_type = other DNA
                        organism = synthetic construct
SEQUENCE: 5
aatagtaaat tgatttaaaa atttcataaa tgcta                                   35

SEQ ID NO: 6            moltype = DNA  length = 33
FEATURE                 Location/Qualifiers
misc_feature            1..33
                        note = Chemically synthesized
source                  1..33
                        mol_type = other DNA
                        organism = synthetic construct
SEQUENCE: 6
tagtaaattg atttaaaaat ttcataaatg cta                                     33

SEQ ID NO: 7            moltype = DNA  length = 35
FEATURE                 Location/Qualifiers
misc_feature            1..35
                        note = Chemically synthesized
source                  1..35
                        mol_type = other DNA
                        organism = synthetic construct
SEQUENCE: 7
aatagtaaat tgattatttc ataaatgcta cataa                                   35

SEQ ID NO: 8            moltype = DNA  length = 33
FEATURE                 Location/Qualifiers
misc_feature            1..33
                        note = Chemically synthesized
source                  1..33
                        mol_type = other DNA
                        organism = synthetic construct
SEQUENCE: 8
tagtaaattg attatttcat aaatgctaca taa                                     33

SEQ ID NO: 9            moltype = DNA  length = 30
FEATURE                 Location/Qualifiers
misc_feature            1..30
                        note = Chemically synthesized
source                  1..30
                        mol_type = other DNA
                        organism = synthetic construct
SEQUENCE: 9
aatagtaaat tgattatttc ataaatgcta                                         30

SEQ ID NO: 10           moltype = DNA  length = 28
FEATURE                 Location/Qualifiers
misc_feature            1..28
                        note = Chemically synthesized
source                  1..28
                        mol_type = other DNA
                        organism = synthetic construct
SEQUENCE: 10
tagtaaattg attatttcat aaatgcta                                           28
```

```
SEQ ID NO: 11              moltype = DNA  length = 25
FEATURE                    Location/Qualifiers
misc_feature               1..25
                           note = Chemically synthesized
source                     1..25
                           mol_type = other DNA
                           organism = synthetic construct
SEQUENCE: 11
aaaattgattt aaaaatttca taaat                                               25

SEQ ID NO: 12              moltype = DNA  length = 20
FEATURE                    Location/Qualifiers
misc_feature               1..20
                           note = Chemically synthesized
source                     1..20
                           mol_type = other DNA
                           organism = synthetic construct
SEQUENCE: 12
aaattgatta tttcataaat                                                      20

SEQ ID NO: 13              moltype = DNA  length = 40
FEATURE                    Location/Qualifiers
misc_feature               1..40
                           note = Chemically synthesized
source                     1..40
                           mol_type = other DNA
                           organism = synthetic construct
SEQUENCE: 13
aatagcaaat tgatttaaaa atttcataaa tgctacataa                                40

SEQ ID NO: 14              moltype = DNA  length = 11
FEATURE                    Location/Qualifiers
misc_feature               1..11
                           note = Chemically synthesized
source                     1..11
                           mol_type = other DNA
                           organism = synthetic construct
SEQUENCE: 14
aaaattgattt a                                                              11

SEQ ID NO: 15              moltype = DNA  length = 13
FEATURE                    Location/Qualifiers
misc_feature               1..13
                           note = Chemically synthesized
source                     1..13
                           mol_type = other DNA
                           organism = synthetic construct
SEQUENCE: 15
aaatttcata aat                                                             13

SEQ ID NO: 16              moltype =   length =
SEQUENCE: 16
000

SEQ ID NO: 17              moltype = DNA  length = 11
FEATURE                    Location/Qualifiers
misc_feature               1..11
                           note = Chemically synthesized
source                     1..11
                           mol_type = other DNA
                           organism = synthetic construct
SEQUENCE: 17
atttcataaa t                                                               11
```

SCREENING ARTIFICIAL NUCLEIC ACIDS BY PARTICLE DISPLAY

CROSS REFERENCE TO RELATED APPLICATIONS

This application is a Continuation of U.S. patent application Ser. No. 16/864,703, filed May 1, 2020, which claims priority to U.S. Provisional Application No. 62/842,022, filed May 2, 2019, each of which is hereby incorporated by reference herein in its entirety.

REFERENCE TO A "SEQUENCE LISTING" SUBMITTED AS AN XML FILE

The Sequence Listing written in the XML file titled "206101-0027-01US_SequenceListing.xml"; created on Feb. 10, 2023, and 21,755 bytes in size, is hereby incorporated by reference.

BACKGROUND OF THE INVENTION

Aptamers, nucleic acid molecules that mimic antibodies by folding into shapes with ligand binding affinity (Ellington and Szortak, 1990, Nature 346:818-822), have enormous potential as diagnostic and therapeutic agents (Cho et al., 2009, Annu Rev Anal Chem 2:241-264; Zhou and Rossi, 2017, Nat. Rev. Drug Discov. 16:181-202). Aptamers are generated by in vitro selection or SELEX (systematic evolution of ligands by exponential enrichment) from large libraries of combinatorial sequences (Wilson and Szortak, 1999, Ann. Rev. Biochem. 68:611-647). Similar to natural selection, in vitro selection is a process of selective amplification in which a population of nucleic acid molecules is challenged to bind a desired target or catalyze a chemical reactions. Molecules having a desired fitness are recovered and amplified to generate a new population of molecules that has become enriched in members with a particular activity. Although hundreds of aptamers have been reported in the literature, the vast majority of these sequences are unsuitable for in vivo applications because they are susceptible to digestion by enzymes that degrade DNA and RNA (Keefe et al., 2010, Nat. Rev. Drug Discov. 9:537-550). Even aptamers with modified bases or expanded genetic letters, which have shown tremendous promise in array-based diagnostics or have achieved high target binding affinity, respectively, are prone to nuclease attack (Gold et al., 2010, Plos One, 5: e15004; Kimoto et al., 2013, Nat. Biotechnol. 31:453-457). One exception is Spiegelmers, mirror-image aptamers composed of L-DNA or L-RNA, but such reagents are currently restricted to achiral targets or targets that can be generated by chemical synthesis, which is a very small fraction (<1%) of the human proteome (Vater and Klussmann, 2015, Drug Discov Today, 20:47-155).

Thus, there is a need in the art for novel methods for synthesis of biologically stable aptamers. The present invention satisfies this unmet need by establishing an XNA aptamer particle display format for rapidly screening aptamers composed of artificial genetic polymers (also known as xeno-nucleic acids or XNAs) for high affinity and high specificity to a desired target.

SUMMARY OF THE INVENTION

In one embodiment, the invention relates to a method of producing a monoclonal xeno-nucleic acid aptamer particle (mXNAP) display library comprising: (a) providing a population of particles comprising a plurality of clonal template DNA molecules, each of which comprises a DNA coding region and a fixed sequence primer binding site; (b) ligating a self-priming stem-loop forming hairpin DNA molecule to the 3' end of the template DNA molecules; (c) extending the 3' end of the self-priming stem-loop in the presence of a polymerase capable of synthesizing an XNA from a DNA template and one or more XNA triphosphate molecules (xNTPs) to form a population of particles comprising clonal double stranded XNA-DNA hybrid molecules; (d) contacting the double stranded XNA-DNA display templates with a primer which anneals to the loop region of the stem-loop structure; and (e) extending the DNA primer using dNTPs and a DNA polymerase to displace the XNA portion of the XNA-DNA display templates to form a population of mXNAP display particles comprising a plurality of clonal nucleic acid molecules comprising a dsDNA region and a single-stranded XNA region.

In one embodiment, the mXNAP library is a mTNAP, mHNAP, mCeNAP, mLNAP, mANAP, mphNAP, or mFANAP library.

In one embodiment, the polymerase capable of synthesizing an XNA from a DNA template and one or more XNA triphosphate molecules (xNTPs) is Kod-RSGA, Kod-RS, Kod-RI, Therminator, pol6G12_521L, pol6G12, polC7, polD4K, PGV2, D4K enzyme, 9oN DNA polymerase, Tgo DNA polymerase, Kod DNA polymerase or Deep vent DNA polymerase.

In one embodiment, the invention relates to a mXNAP display library comprising a population of display particles, wherein each display particle comprises a plurality of clonal nucleic acid molecules comprising a dsDNA region and a single-stranded XNA aptamer region.

In one embodiment, the mXNAP library is a mTNAP, mHNAP, mCeNAP, mLNAP, mANAP. mphNAP, or mFANAP library.

In one embodiment, the mXNAP display library of comprises at least $10^5$ mXNAPs.

In one embodiment, the invention relates to a method of screening for an XNA aptamer having a desired property, comprising the steps of: (a) incubating a mXNAP display library comprising a population of display particles, wherein each display particle comprises a plurality of clonal nucleic acid molecules comprising a dsDNA region and a single-stranded XNA aptamer region with at least one candidate interaction partner for an amount of time sufficient for interaction of the XNA aptamer regions with the candidate interaction partner; and (b) selecting mXNAP particles displaying XNA aptamers that have the desired property.

In one embodiment, the desired property is selected from the group consisting of a target binding activity and a target-binding induced activity.

In one embodiment, the invention relates to an XNA aptamer identified through screening a mXNAP library as having a desired property. In one embodiment, the aptamer is a TNA aptamer, a HNA aptamer, a CeNA aptamer, a LNA aptamer, an ANA aptamer or a FANA aptamer.

In one embodiment, the invention relates to a pharmaceutical composition comprising an XNA aptamer identified through screening a mXNAP library as having a desired property. In one embodiment, the composition further comprising a pharmaceutically acceptable excipient.

In one embodiment, the invention relates to a method of treating a disease or disorder in a subject in need thereof, comprising administering to the subject an effective amount of a pharmaceutical composition comprising an XNA aptamer identified through screening a mXNAP library as having a desired property.

In one embodiment, the invention relates to a TNA aptamer, comprising a sequence selected from SEQ ID NO:1 to SEQ ID NO:3, a variant of SEQ ID NO:1 to SEQ ID NO:3, or a fragment comprising at least 20 nt of SEQ ID NO:1 to SEQ ID NO:3.

In one embodiment, the invention relates to a pharmaceutical composition comprising a TNA aptamer, comprising a sequence selected from SEQ ID NO:1 to SEQ ID NO:3, a variant of SEQ ID NO:1 to SEQ ID NO:3, or a fragment comprising at least 20 nt of SEQ ID NO:1 to SEQ ID NO:3. In one embodiment, the composition further comprising a pharmaceutically acceptable excipient.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 4A depicts the chemical structure for the linearized backbone of RNA and α-L-threofuranosyl nucleic acid (TNA). FIG. 4B depicts an in vitro selection strategy designed to isolate TNA aptamers against HIV reverse transcriptase. A chemically synthesized DNA library encoding 40 random nucleotide positions flanked on both sides with fixed-sequence primer-binding sites is ligated onto a DNA stem-loop. The pool of self-priming DNA templates is extended with tNTPs to produce a population of TNA-DNA hairpin structures. A separate DNA primer modified with a 5' IR dye is annealed to the loop region and extended with DNA to displace the TNA strand. The resulting pool of TNA-dsDNA fusion molecules is incubated with the target protein immobilized on Ni-NTA beads, washed to remove non-functional molecules, recovered, and amplified by PCR. The dsDNA is made single-stranded and then used to initiate another round of selection and amplification. FIG. 4C depicts MST binding affinity curves obtained for the top three TNA aptamers identified after 3 rounds of in vitro selection. HIV-RT Aptamer 3.17 was evaluated in triplicate. Error bars, standard deviation of each data point.

FIG. 5A depicts the binding validation. The solution binding affinities (KD) of HIV-RT aptamer 3.17 and a known DNA aptamer were validated by native polyacrylamide gel electrophoresis. FIG. 5B depicts the biological stability. Binding isotherms obtained in the presence of SVPE for the TNA and DNA aptamers. FIG. 5C depicts the time-dependent nuclease stability profiles. IR-labeled DNA and TNA aptamers were monitored by denaturing polyacrylamide gel electrophoresis following exposure to SVPE. FIG. 5D depicts the thermal stability. HIV-RT aptamer 3.17, a known DNA aptamer, and a commercial monoclonal antibody were challenged to function at room temperature after heating at 70° C. for a period of 0-48 hours.

DETAILED DESCRIPTION

Figure 1:
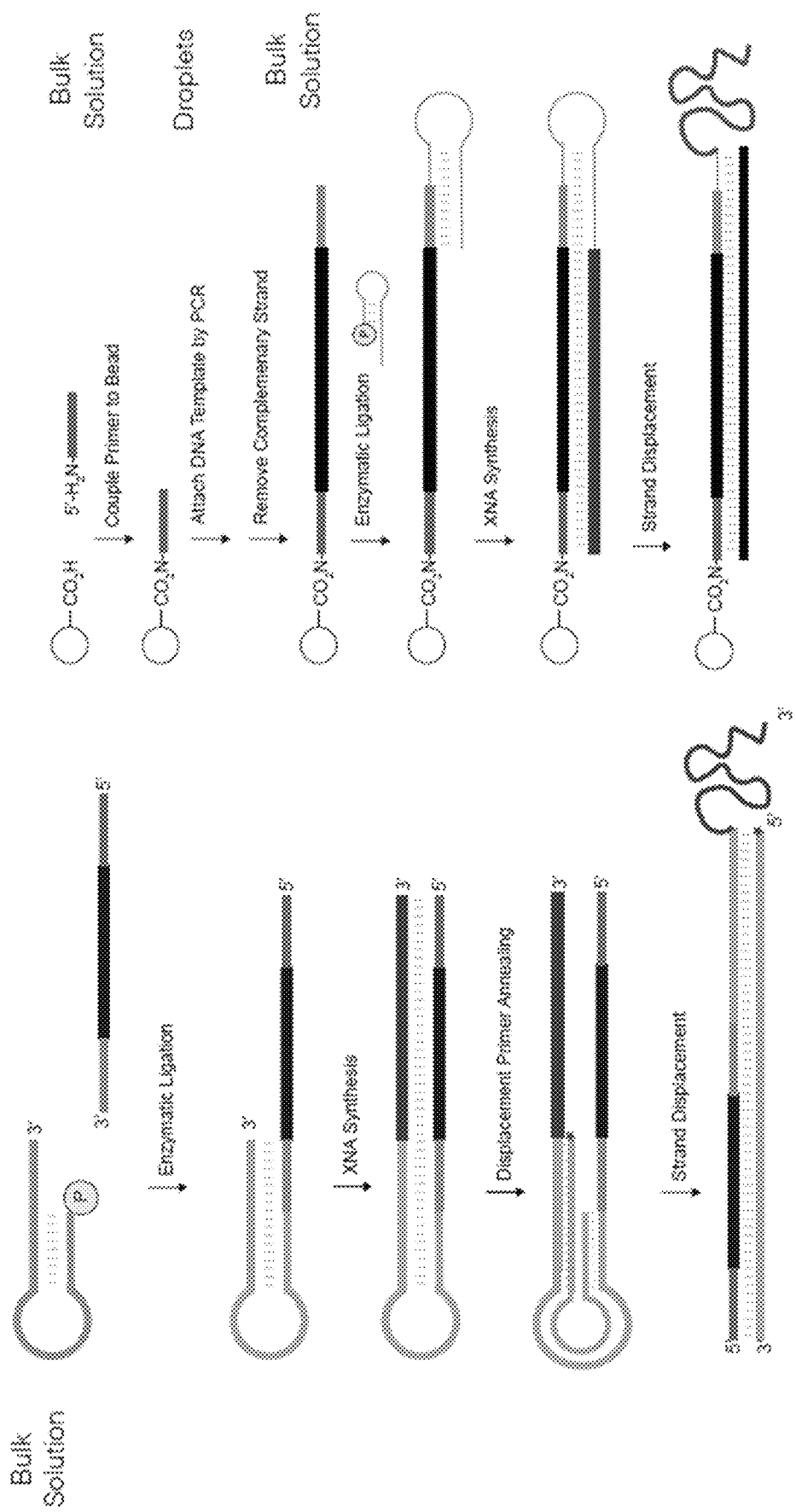
FIG. 1 depicts schematic diagrams of the generation of monoclonal XNA aptamer particles in which many copies of the same XNA aptamer sequence are displayed on the same bead, and the ensemble of beads constitutes a library of XNA aptamer particles for target screening.

In one embodiment, the present disclosure provides methods for generating an artificial nucleic acid, commonly referred to as XNAs or 'xeno-nucleic acids,' particle display library of monoclonal XNA aptamer display particles (mXNAPs), and the use of the display library to screen for aptamers that bind to a target with high specificity.

In one embodiment, the present disclosure provides methods for use of the display library for identifying one or more unnatural nucleic acid agents, e.g., XNA aptamers, having a desired property identified from a mixture of candidate XNA aptamers. The desired property may be a target binding activity or a target-binding induced activity, e.g., a catalytic activity or a modified catalytic activity; inhibition activity, activation activity, or a modification of an inhibition activity or activation activity; structure switching activity or a modification of a structure switching activity; or cooperative activity. In some embodiments, the desired property is a target binding activity or a target-binding induced activity. In some embodiments, the target binding activity is one of affinity, specificity and bi-specificity.

XNA aptamers that can be displayed on the mXNAPs of the invention include, but are not limited to, threose nucleic acid (TNA) aptamers, hexitol nucleic acid (HNA) aptamers, cyclohexene nucleic acid (CeNA) aptamers, locked nucleic acid (LNA) aptamers, arabino nucleic acid (ANA) aptamers, alkyl phosphonate nucleic acid (phNA) aptamers, and 2'-deoxy-2'-fluoroarabinonucleic acid (FANA) aptamers.

In one embodiment, the invention relates to XNA aptamers identified using the screening methods of the invention, compositions comprising the identified XNA aptamers and methods of use for the treatment of a disease or disorder.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass non-limiting variations of ±40% or ±20% or ±10%, ±5%, ±1%, or ±0.1% from the specified value, as such variations are appropriate.

As used herein the term "aptamer" or "aptamer sequence" refers to a nucleic acid having a specific binding affinity for a target, e.g., a target molecule, wherein such target is other than a polynucleotide that binds to the aptamer or aptamer sequence through a mechanism which predominantly depends on Watson/Crick base pairing.

A "natural" nucleoside is one that occurs in nature. For the purposes of this invention the following nucleosides are defined as the natural nucleosides: adenosine, cytidine, guanosine, uridine, 2'-deoxyadenosine, 2'-deoxycytidine, 2'-deoxyguanosine, thymidine, and inosine.

The term base, unless otherwise specified, refers to the base moiety of a nucleoside or nucleotide (a nucleobases). The base moiety is the heterocycle portion of a nucleoside or nucleotide. The base moiety may be a pyrimidine derivative or analog, a purine derivative or analog, or other heterocycle. The nucleoside base may contain two or more nitrogen atoms and may contain one or more peripheral substituents. The nucleoside base is attached to the sugar moiety of the nucleotide mimic in such ways that both β-D- and β-L-nucleoside and nucleotide can be produced.

The term sugar refers to the ribofuranose of deoxyribofuranose portion of a nucleoside or nucleotide. The sugar moiety may contain one or more substituents at the C1-, C2-, C3-, C4-, and C5-position of the ribofuranose. Substituents may direct to either the α- or β-face of the ribofuranose. The nucleoside base that can be considered as a substituent at the C-1 position of the ribofuranose directs to the β-face of the sugar. The β-face is the side of a ribofuranose on which a purine or pyrimidine base of natural β-D-nucleosides is present. The α-face is the side of the sugar opposite to the β-face. The sugar moiety of the present invention is not limited to a ribofuranose and its derivatives, instead, it may be a carbohydrate, a carbohydrate analog, a carbocyclic ring, or other ribofuranose analog.

The term sugar-modified nucleoside refers to a nucleoside containing a modified sugar moiety.

The term base-modified nucleoside refers to a nucleoside containing a modified base moiety, relative to a base moiety found in a natural nucleoside.

As used herein, the term "nucleic acid" refers to both naturally-occurring molecules such as DNA and RNA, but also various derivatives and analogs. Generally, the probes, hairpin linkers, and target polynucleotides of the present teachings are nucleic acids, and typically comprise DNA. Additional derivatives and analogs can be employed as will be appreciated by one having ordinary skill in the art.

The term "nucleotide base", as used herein, refers to a substituted or unsubstituted aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases adenine, guanine, cytosine, 6 methyl-cytosine, uracil, thymine, and analogs of the naturally occurring nucleotide bases, e.g., 7-deazaadenine, 7-deazaguanine, 7-deaza-8-azaguanine, 7-deaza-8-azaadenine, N6 delta 2-isopentenyladenine (6iA), N6-delta 2-isopentenyl-2-methylthioadenine (2 ms6iA), N2-dimethylguanine (dmG), 7methylguanine (7mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, 06-methylguanine, N6-methyladenine, 04-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman, 1989, Practical Handbook of Biochemistry and Molecular Biology, pp. 385-394, CRC Press, Boca Raton, Fla., and the references cited therein.

The term "nucleotide", as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR2 or halogen groups, where each R is independently H, C1-C6 alkyl or C5-C14 aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-anomeric nucleotides, 1'-anomeric nucleotides, 2'-4'- and 3'-4'-linked and other "locked" or "LNA", bicyclic sugar modifications (see, e.g., PCT published application nos. WO 98/22489, WO 98/39352; and WO 99/14226). The term "nucleic acid" typically refers to large polynucleotides.

The term "nucleotide analogs" as used herein refers to modified or non-naturally occurring nucleotides including, but not limited to, analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner and herein incorporated by reference); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242; B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include nucleotides having modification on the sugar moiety, such as dideoxy nucleotides and 2'-O-methyl nucleotides. Nucleoside analogue examples wherein the natural sugar moiety is modified include but are not limited to hexitol nucleic acid (HNA), cyclohexene nucleic acids (CeNA), locked nucleic acids (LNA), altritol nucleic acids (ANA) and peptide nucleic acids (PNA). Nucleotide analogs include modified forms of deoxyribo-nucleotides as well as ribonucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning and amplification technology, and the like, and by synthetic means. An "oligonucleotide" as used herein refers to a short polynucleotide, typically less than 100 bases in length.

As used herein, the term "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

The term "reaction mixture" as used herein refers to a fluid medium in which a target is contacted with or in contact with candidate nucleic acid agents, e.g., candidate aptamer sequences. This includes, for example, a reaction mixture in which a library of candidate nucleic acid agents, e.g., aptamer sequences, is initially contacted with a target and any subsequent wash steps designed to remove non-specific or low-affinity target binding agents. Where desired, the stringency conditions of the reaction mixture can be modified so as to influence the formation of complexes between the target and the candidate nucleic acid agents, e.g., candidate aptamer sequences. Thus, for example, stringency conditions of a reaction mixture during initial contacting of target and a library of candidate nucleic acid agents, e.g., candidate aptamer sequences, (which may be referred to as "binding conditions") and stringency conditions of a reaction mixture during washing (referred to as "wash conditions", e.g., to disrupt complexes of an undesirably low affinity and/or deplete non-specifically bound candidate nucleic acid agents) may be of the same or different stringencies.

The term xeno-nucleic acid, abbreviated XNA, refers to a nucleic acid polymer in which the natural ribose and deoxyribose sugars found in RNA and DNA replaced with another natural or unnatural sugar moiety. Examples include but are not limited to α-L-threofuranosyl nucleic acid (TNA), hexitol nucleic acid (HNA), arabino nucleic acid (ANA). XNAs are not recognized by natural DNA and RNA polymerases, and therefore require engineered polymerases for their synthesis.

The term aptamer particle, also known as monoclonal aptamer particle, refers to a bead that contains many copies of the same aptamer sequence.

The term XNA aptamer particle refers to an aptamer particle that contains many copies of the same XNA aptamer sequence.

The term XNA libraries refers to a combinatorial library of XNA molecules having different sequence compositions.

The terms "specific binding," "specifically bind," and the like, refer to the ability of a first binding molecule or moiety to preferentially bind (covalently or non-covalently) to a second binding molecule or moiety relative to other molecules or moieties in a reaction mixture.

A "therapeutic" treatment is a treatment administered to a subject who exhibits signs of pathology, for the purpose of diminishing or eliminating those signs.

As used herein, "TNA" or "TNAs" refer to nucleic acids having a backbone composed primarily of α-L-threofuranosyl-(3'→2') (threose)-containing nucleotides, but may include heteropolymers comprising both tNTPs and dNTPs (e.g., dC).

As used herein, "tNTPs" refer to threose nucleotide triphosphates.

As used herein, "tNTP analog" refers to a threose nucleotide triphosphate having a modified base moiety.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a sign or symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the terms "effective amount," "pharmaceutically effective amount" and "therapeutically effective amount" refer to a nontoxic but sufficient amount of an agent to provide the desired biological result. That result may be reduction and/or alleviation of a sign, a symptom, or a cause of a disease or disorder, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing an undesirable biological effect or interacting in a deleterious manner with any of the components of the composition in which it is contained.

As used herein, the language "pharmaceutically acceptable salt" refers to a salt of the administered compound prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present disclosure provides methods for identifying one or more unnatural nucleic acid agents, e.g., xeno-nucleic acid (XNA) aptamers, having a desired property identified from a mixture of candidate XNA aptamers. The method generally includes generating a population of monoclonal XNA display particles, wherein multiple clonal copies of a single XNA aptamer are immobilized on any one of the particles, and wherein the population represents multiple unique monoclonal XNA display particles (mXNAPs). The particles are exposed to a target, and particles including candidate nucleic acid agents having the desired property are isolated. In this way, one or more nucleic acid agents having the desired property may be identified.

The desired property may be a target binding activity or a target-binding induced activity, e.g., a catalytic activity or a modified catalytic activity; inhibition activity, activation activity, or a modification of an inhibition activity or activation activity; structure switching activity or a modification of a structure switching activity; or cooperative activity. In some embodiments, the desired property is a target binding activity or a target-binding induced activity. In some embodiments, the target binding activity is one of affinity, specificity and bi-specificity.

The present disclosure also provides a quantitative, particle-based method of generating and screening candidate XNA aptamers. Generally, a library of mXNAPs is prepared, wherein each mXNAPs displays multiple copies of a unique candidate XNA aptamer sequence on its surface. The mXNAPs are exposed to one or more target and each mXNAP is sorted based on a quantitative analysis of an interaction between the candidate aptamer sequences on the mXNAP and the target. Following sorting, an enriched pool of mXNAPs may be provided which has reduced sequence diversity relative to the original library. One or more rounds of screening may be performed to identify XNA aptamers having desired target interactions.

In one embodiment, the invention relates to methods of screening a library of XNA aptamers to identify aptamers having a desired property (e.g., high affinity for a target). XNA aptamers that can be displayed on the mXNAPs of the invention include, but are not limited to, threose nucleic acid (TNA) aptamers, hexitol nucleic acid (HNA) aptamers, cyclohexene nucleic acid (CeNA) aptamers, locked nucleic acid (LNA) aptamers, arabino nucleic acid (ANA) aptamers, glycerol nucleic acid (GNA), alkyl phosphonate nucleic acid (phNA) aptamers, and 2'-deoxy-2'-fluoroarabinonucleic acid (FANA) aptamers. The invention should not be limited to the exemplary XNA's listed herein. Rather, the invention includes any XNA including but not limited to XNA's currently available and XNA's that will become available.

In one embodiment, the invention relates to mXNAP display libraries for use in the screening methods of the invention and to XNA aptamers identified using the screening methods of the invention. In various embodiments, the invention relates to pharmaceutical compositions comprising the identified XNA aptamers and methods of use for the treatment of a disease or disorder.

Nucleoside Triphosphates and Nucleic Acids

In one embodiment, the invention relates to nucleic acid molecules containing one or more nucleoside triphosphate analog or isomer (xNTPs). In one aspect, nucleoside triphosphate analogs or isomers can be incorporated into nucleic acid molecules including, but not limited to oligonucleotides, aptamers, deoxyribonucleic acid (DNA), ribonucleic acid (RNA) and peptide nucleic acid (PNA). A nucleic acid of the invention also includes artificial nucleic acid polymers, commonly referred to as XNAs or 'xeno-nucleic acids' where the backbone structure contains a sugar other than ribose or deoxyribose. While some of these molecules can be considered natural derivatives of RNA, like arabino nucleic acid (ANA), threose nucleic acid (TNA), and glycerol nucleic acid (GNA), others are completely unnatural, like locked nucleic acid (LNA), cyclohexene nucleic acid (CeNA), and hexitol nucleic acid (HNA).

Therefore, in one embodiment, the invention provides artificial or synthetic nucleic acid molecules in which one or more nucleoside triphosphate analog is incorporated. The length of the nucleic acids may vary. The nucleic acids may be modified, e.g. may comprise one or more modified nucleobases or modified sugar moieties (e.g., comprising methoxy groups). The backbone of the nucleic acid may comprise one or more peptide bonds as in peptide nucleic acid (PNA). The nucleic acid may comprise a base analog such as non-purine or non-pyrimidine analog or nucleotide analog. It may also comprise additional attachments such as proteins, peptides and/or or amino acids.

In one embodiment, the XNA aptamers of the invention are TNA aptamers, containing one or more α-L-threofuranosyl nucleoside triphosphate (tNTP). tNTPs that can be included in a TNA aptamer of the invention include, but are not limited to, 1-(α-L-threofuranosyl)thymidine-3'-triphosphate (tTTP), 1-(α-L-threofuranosyl)cytidine-3'-triphosphate (tCTP), 9-(α-L-threofuranosyl)adenosine-3'-triphosphate (tATP), and 9-(α-L-threofuranosyl)guanosine-3'-triphosphate (tGTP).

In various embodiments, the XNA aptamers of the invention are HNA aptamers, containing one or more 1',5'-anhydrohexitol nucleoside triphosphates (hNTPs), CeNA aptamers, containing one or more cyclohexenyl nucleoside triphosphate (CeNTP), LNA aptamers, containing one or more locked nucleic acid nucleoside triphosphates (lNTP), ANA aptamers, containing one or more arabino nucleoside triphosphates (lNTP), phNA aptamers, containing one or more P-α-ethyl phosphonyl-β,γ-diphosphate nucleoside triphosphate (P-Et-phNTP) or P-α-methyl phosphonyl-β,γ-diphosphate (P-Met-phNTP), and FANA aptamers, containing one or more 2'-deoxy-2'-fluoroarabino nucleoside triphosphates (faNTP). The invention should not be limited to the exemplary XNA's listed herein. Rather, the invention includes any XNA including but not limited to XNA's currently available and XNA's that will become available.

In one embodiment, the TNA aptamer of the invention comprises a TNA sequence as set forth in SEQ ID NO:1 through SEQ ID NO:3.

In some embodiments, the aptamer can be labeled. Examples of possible labels include, but are not limited to a radioisotope, an enzyme, an enzyme cofactor, an enzyme substrate, an enzyme inhibitor, a dye, a hapten, a chemiluminescent molecule, a fluorescent molecule, a phosphorescent molecule, an electrochemiluminescent molecule, a chromophore, a magnetic particle, an affinity label, a chromogenic agent, an azide group or other groups used for click chemistry, and other moieties known in the art.

TNA Oligonucleotides

In one embodiment, the invention provides biologically stable TNA oligonucleotides, wherein the TNA oligonucleotides comprise an effective amount of TNA and is completely resistant to enzymatic degradation. As used herein, by "effective amount of TNA" means an amount of TNA sufficient to yield resistance to enzymatic degradation. In one embodiment, the effective amount of TNA may comprise at least one TNA nucleic acid. In another embodiment, the effective amount of TNA may comprise at least two TNA nucleic acids. In other embodiments, the effective amount of TNA may comprise at least four TNA nucleic acids, at least five TNA nucleic acids, at least six TNA nucleic acids, at least seven TNA nucleic acids, at least ten nucleic acids.

As used herein, "resistant to enzymatic degradation" means the XNA oligonucleotide of the present invention resists degradation by enzymes including, without limitation, human liver microsomes, snake venom phosphodiesterase, RNAse A, RQ1 DNAse, and Turbo DNAse, for at least 24 hours.

In one embodiment, the invention provides stable, nuclease-resistant TNA-DNA oligonucleotides, wherein the TNA-DNA oligonucleotides comprise an effective amount of TNA and is resistant to enzymatic degradation. In one embodiment, the effective amount of TNA may comprise at least one TNA nucleic acid.

In one embodiment, the TNA aptamer of the invention comprises a TNA sequence as set forth in SEQ ID NO:1 through SEQ ID NO:3 (Table 1), or a fragment, derivative or variant thereof. In one embodiment, the TNA aptamer is a fragment comprising at least 20, 25, 30, 35 or at least 40 nt of SEQ ID NO:1 through SEQ ID NO:3. In one embodiment, the TNA aptamer is a variant comprising a TNA sequence having at least 50, 55, 60, 65, 70, 75, 80, 85, 90, 95, 96, 97, 98 or 99% identity to SEQ ID NO:1 through SEQ ID NO:3.

TABLE 1

HIV-RT binding TNA aptamers

| SEQ ID NO | Sequence | Description |
|---|---|---|
| 1 | atagcaaattacttataaat tagttcagtagctactgtca | HIV-RT 3.10 |
| 2 | agcaaagtccttggaatacg atcgtaccgttcctagacta | HIV-RT 3.15 |
| 3 | aatagtaaattgatttaaaa atttcataaatgctacataa | HIV-RT 3.17 |

In another embodiment, the invention provides a method of preparing nuclease-resistant TNA-DNA oligonucleotides, the method comprising contacting a self-priming, stem-loop forming template DNA molecule with a TNA polymerase and at least one tNTP in appropriate conditions such that the polymerase to synthesize nascent TNA from the priming end of the DNA molecule complementary to the template region of the DNA molecule, to yield a TNA-DNA hybrid oligonucleotide.

In some embodiments, the effective amount of TNA in a TNA-DNA oligonucleotide is at least one TNA. In some embodiments, the effective amount of TNA in a TNA-DNA oligonucleotide is at least two TNA, at least three TNA, at least four TNA, at least 5 TNA, at least 6 TNA, at least 7 TNA, at least 8 TNA, at least 9 TNA, at least 10 TNA, at least 15 TNA, at least 20 TNA, at least 25 TNA, at least 30 TNA, at least 35 TNA, at least 40 TNA and may contain any number of TNA inbetween.

In some embodiments, the effective amount of TNA in a TNA-DNA oligonucleotide is at least 1% of the oligomers, at least 2% of the oligomers, at least 5%, or at least 7% of the oligomers. In some embodiments, the effective amount of TNA in the TNA-DNA oligonucleotide is at least 10% of the oligomers, at least 15% of the oligomers, at least 20% of the oligomers, at least 25% of the oligomers, at least 30% of the oligomers, at least 35% of the oligomers, at least 40% of the oligomers, at least 50% of the oligomers, at least 60% of the oligomers, at least 70% of the oligomers, at least 80% of the oligomers and any amounts or ranges inbetween (for example, 6%, 7%, 8%, 9%, 11%, 12%, 13%, 14%, 15%, 17%, 18%, 19%, 21%, 22%, 23%, 24%, 26%, 26%, 27%, 28%, 29%, 31%, 32%, 33%, 42%, 55%, 58%, 66% etc. etc.).

In another embodiment, the invention provides methods of using the nuclease-resistant TNA and TNA-DNA oligonucleotides of the present invention. The nuclease-resistant TNA and TNA-DNA oligonucleotides of the present invention may be used as a therapeutic (antisense, catalyst, RNAi etc), affinity reagent (aptamer, ribozyme) for diagnostic drug delivery, diagnostic testing, imaging etc. In various embodiments, the nuclease-resistant TNA and TNA-DNA oligonucleotides of the present invention may be substituted in part or in whole for any application that currently uses DNA or RNA.

mXNAP Display Library

Candidate nucleic acid agents and candidate aptamers for use in a screen of the invention may be provided in the form of an mXNAP display library which includes a large number of display particles, wherein each particle is linked to a) template DNA molecules comprising a region having a random nucleic acid sequence, which encodes an XNA aptamer, or b) dsDNA-XNA hybrid molecules wherein the XNA oligonucleotide comprises an XNA aptamer. mXNAP display libraries may include, for example, from about $1 \times 10^2$ to about $1 \times 10^{14}$ unique template DNA sequences or from about $1 \times 10^2$ to about $1 \times 10^{14}$ unique candidate XNA aptamer sequences, e.g., from about $1 \times 10^3$ to about $1 \times 10^{14}$ unique sequences, from about $1 \times 10^4$ to about $1 \times 10^{14}$ unique sequences, from about $1 \times 10^5$ to about $1 \times 10^{14}$ unique sequences, from about $1 \times 10^6$ to about $1 \times 10^{14}$ unique sequences, from about $1 \times 10^7$ to about $1 \times 10^{14}$ unique sequences, from about $1 \times 10^8$ to about $1 \times 10^{14}$ unique sequences, from about $1 \times 10^9$ to about $1 \times 10^{14}$ unique sequences, from about $1 \times 10^{10}$ to about $1 \times 10^{14}$ unique sequences, from about $1 \times 10^{11}$ to about $1 \times 10^{14}$ unique sequences, from about $1 \times 10^{12}$ to about $1 \times 10^{14}$ unique sequences, or from about $1 \times 10^{13}$ to about $1 \times 10^{14}$ unique sequences.

XNA aptamer encoding sequences or XNA aptamers displayed on the mXNAPs of the invention may be, for example, from about 30 to about 150 nucleotides in length, e.g., from about 40 to about 130 nucleotides in length, from about 50 to about 120 nucleotides in length, from about 60 to about 110 nucleotides in length, from about 70 to about 100 nucleotides in length, or from about 80 to about 90 nucleotides in length. Candidate nucleic acid agents and candidate aptamers including nucleic acid sequences may include random nucleic acid sequences of from about 30 nucleotides in length to about 70 nucleotides in length, e.g., from about 40 nucleotides in length to about 60 nucleotides in length. In addition to random nucleic acid sequence regions, template DNA sequences and XNA sequences may may include flanking regions containing primer binding sites.

Particles

A variety of suitable particles may be used in the generation of the mXNAP display library as described herein. Such particles may be sized to have at least one dimension, e.g., diameter, of from about 50 nm to about 100 μm. For example, in some embodiments a suitable particle is sized to have at least one dimension of from about 50 nm to about 1 μm, e.g., from about 50 nm to about 500 nm, or from about 50 nm to about 100 nm. In other embodiments, a suitable particle is sized to have at least one dimension of from about 500 nm to about 100 μm, e.g., from about 1 μm to about 100 μm, or from about 50 μm to about 100 μm. Suitable particles may be generally spherical or may have any other suitable shape.

Particles may be made from a variety of suitable materials known in the art. For example, magnetic particles may be utilized in the disclosed methods and compositions. Suitable magnetic particles may include, for example, magnetic beads or other small objects made from a magnetic material such as a ferromagnetic material, a paramagnetic material, or a superparamagnetic material. Magnetic particles may include, e.g., iron oxide ($Fe_2O_3$ and/or $Fe_3O_4$). Additional particles of interest may include polymer-based particles, e.g., polymer based beads. For example, polystyrene particles may be utilized. In addition, in some embodiments ceramic particles may be utilized.

The particles may include or be coated with a material which facilitates coupling of the particles to candidate nucleic acid agents and candidate aptamer sequences. Examples of coatings include polymer shells, glasses, ceramics, gels, etc. In some embodiments, the coatings include or are themselves coated with a material that facilitates coupling or physical association of the particles with the candidate nucleic acid agent sequences and candidate aptamer sequences. For example, particles with exposed carboxylic acid groups may be used for attachment to candidate nucleic acid agents and candidate aptamers.

Suitable particles may include one or more functional groups, e.g., one or members of a reactive pair as described herein, positioned on one or more surfaces of the particles. Suitable functional groups may include, for example, amine groups, carboxyl groups, thiol groups, $SiO_2$, EDTA, and boronic acid functional groups.

In some embodiments, suitable particles may include one or more members of a specific binding pair on one or more surfaces of the particles. For example, avidin, streptavidin, Neutravidin®, Captavidin™, or biotin may be positioned on one or more surfaces of the particles.

Methods of Attaching Candidate Nucleic Acid Agents and Candidate Aptamer Sequences to Particles A variety of methods may be used to attach nucleic acid molecules (e.g., primer sequences), to particles for use in generating mXNAPs as described herein.

In one suitable method nucleic acid molecules may be attached to a particle having exposed carboxylic acid groups using amino group modification. For example, 5'-amino modified oligonucleotides may be used in connection with carbodiimide mediated amide bond formation to attach the oligonucleotide sequences to particles.

Carbodiimide mediated coupling methods are described in greater detail, for example, in Nakajima N. and Ikade Y. (1995) Bioconjugate Chem., 6(1):123-130; Gilles et al. (1990) Anal Biochem., 184(2):244-248; Sehgal D. and Vijay I K. (1994) Anal Biochem. 218(1):87-91; and Szajani et al. (1991) Appl Biochem Biotechnol. 30(2):225-231.

DNA Display

DNA display is a method in which XNA-DNA fusion molecules are generated in which a newly transcribed XNA oligonucleotide is linked to its corresponding DNA template. This is achieved by using a self-priming stem-loop forming DNA molecule which is ligated to a single stranded DNA molecule comprising a template region for the synthesis of the desired XNA oligonucleotide.

When the DNA display template is replicated, xNTPs are incorporated into the newly-synthesized portion of the molecule by an XNA polymerase. The XNA region is then displaced from the template molecule resulting in a DNA-XNA fusion molecule.

In one embodiment, tNTPs are incorporated into the newly-synthesized portion of the molecule by a TNA polymerase. The TNA region is then displaced from the template molecule resulting in a DNA-TNA fusion molecule. Exemplary TNA polymerases that can be used in the methods of the invention include, but are not limited to, Kod-RSGA, Kod-RS, Kod-RI, and Terminator TNA polymerase.

In one embodiment, hNTPs are incorporated into the newly-synthesized portion of the molecule by a polymerase capable of synthesizing HNA from a DNA template. The HNA region is then displaced from the template molecule resulting in a DNA-HNA fusion molecule. Exemplary polymerases capable of synthesizing HNA from a DNA template that can be used in the methods of the invention include, but are not limited to, pol6G12_521L polymerase.

In one embodiment, CeNTPs are incorporated into the newly-synthesized portion of the molecule by a polymerase capable of synthesizing CeNA from a DNA template. The CeNA region is then displaced from the template molecule resulting in a DNA-CeNA fusion molecule. Exemplary polymerases capable of synthesizing CeNA from a DNA template that can be used in the methods of the invention include, but are not limited to, pol6G12, polC7 and polD4K polymerase.

In one embodiment, lNTPs are incorporated into the newly-synthesized portion of the molecule by a polymerase capable of synthesizing LNA from a DNA template. The LNA region is then displaced from the template molecule resulting in a DNA-LNA fusion molecule. Exemplary polymerases capable of synthesizing LNA from a DNA template that can be used in the methods of the invention include, but are not limited to, polC7 and polD4K polymerase.

In one embodiment, aNTPs are incorporated into the newly-synthesized portion of the molecule by a polymerase capable of synthesizing ANA from a DNA template. The ANA region is then displaced from the template molecule resulting in a DNA-ANA fusion molecule. Exemplary polymerases capable of synthesizing ANA from a DNA template that can be used in the methods of the invention include, but are not limited to, polC7 and polD4K polymerase.

In one embodiment, phNTPs are incorporated into the newly-synthesized portion of the molecule by a polymerase capable of synthesizing ANA from a DNA template. The phNA region is then displaced from the template molecule resulting in a DNA-phNA fusion molecule. Exemplary polymerases capable of synthesizing phNA from a DNA template that can be used in the methods of the invention include, but are not limited to, PGV2 polymerase.

In one embodiment, faNTPs are incorporated into the newly-synthesized portion of the molecule by a polymerase capable of synthesizing FANA region is then displaced from the template molecule resulting in a DNA-FANA fusion molecule. Exemplary polymerases capable of synthesizing FANA from a DNA template that can be used in the methods of the invention include, but are not limited to, D4K enzyme, 9oN DNA polymerase, Tgo DNA polymerase, Kod DNA polymerase and Deep vent DNA polymerase.

The DNA from a selected DNA-XNA fusion can be amplified, and ligated to a hairpin forming DNA molecule ready for the next round of selection. The ability to carry out multiple rounds of selection and amplification enables the enrichment and isolation of very rare molecules, e.g., one desired molecule out of a pool of $10^{13}$ members. This in turn allows the isolation of new or improved XNA or XNA aptamers which can specifically recognize a target or which can catalyze desired chemical reactions.

In one aspect, described herein is a method of making a DNA display library displaying TNA, HNA, CeNA, LNA, ANA, phNA or FANA aptamers, or a combination thereof. In certain embodiments, the DNA display library comprises molecules for the display of at least $10^5$, $10^6$, $10^7$, $10^8$, $10^9$, $10^{10}$, $10^{11}$, $10^{12}$, $10^{13}$, or at least $10^{14}$ different XNA aptamers.

In one aspect, provided herein is a method of preparing a DNA display library comprising the steps of: (a) providing a population of self-priming, stem-loop forming, template DNA molecules, each of which comprises a stem-loop forming priming sequence, a random DNA coding region and a fixed sequence primer binding site; (b) extending the primer in the presence of an XNA polymerase and one or more XNA triphosphate molecules (xNTPs) to form a population of double stranded XNA-DNA display templates; and (c) contacting the double stranded XNA-DNA display templates with a primer which anneals to the loop region of the stem-loop structure and extending the DNA primer using dNTPs and a DNA polymerase to displace the XNA portion of the XNA-DNA display templates to form a population of display molecules comprising a dsDNA region and a single-stranded XNA region (dsDNA-ssXNA fusion display molecule).

Particle Display

In one embodiment, the invention provides a method of generating a monoclonal XNA-particle (mXNAP) display library. In one embodiment, the mXNAPs of the invention are generated by coupling the 5' end of a single stranded DNA molecule comprising a DNA template region for the synthesis of the desired XNA oligonucleotide.

In one embodiment, the template DNA molecule can be attached to the particles using emulsion PCR methods prior to ligation to the hairpin forming DNA molecule. Generally, emulsion PCR as used in connection with the disclosed methods isolates individual template DNA molecules, e.g., from a combinatorial library, along with primer-coated particles, e.g., beads, in aqueous droplets within an oil phase. PCR amplification then coats each bead with clonal copies of the DNA molecule. After breaking the emulsion and removing unreacted PCR reagents, hybridized strands may be de-hybridized and the template particles collected for subsequent ligation to a self-priming DNA hairpin molecule. In one embodiment, the XNA is then generated by contacting the ligated template particles with a reaction mixture containing at least one xNTP and at least one polymerase capable of synthesizing XNA from a DNA template (an XNA polymerase).

When the DNA display template is copied, xNTPs are incorporated into the newly-synthesized portion of the molecule by the XNA polymerase. The XNA region is then displaced from the template molecule resulting in a DNA-XNA fusion molecule coupled to the particle.

In one embodiment, tNTPs are incorporated into the newly-synthesized portion of the molecule by a TNA polymerase. The TNA region is then displaced from the template molecule resulting in a DNA-TNA fusion molecule. The resultant display library is a mTNAP library. Exemplary TNA polymerases that can be used in the methods of the invention include, but are not limited to, Kod-RSGA, Kod-RS, Kod-RI, and Terminator TNA polymerase.

In one embodiment, hNTPs are incorporated into the newly-synthesized portion of the molecule by a polymerase capable of synthesizing HNA from a DNA template. The HNA region is then displaced from the template molecule resulting in a DNA-HNA fusion molecule. The resultant display library is a mHNAP library. Exemplary polymerases capable of synthesizing HNA from a DNA template that can be used in the methods of the invention include, but are not limited to, pol6G12_521L polymerase.

In one embodiment, CeNTPs are incorporated into the newly-synthesized portion of the molecule by a polymerase capable of synthesizing CeNA from a DNA template. The CeNA region is then displaced from the template molecule resulting in a DNA-CeNA fusion molecule. The resultant display library is a mCeNAP library. Exemplary polymerases capable of synthesizing CeNA from a DNA template that can be used in the methods of the invention include, but are not limited to, pol6G12, polC7 and polD4K polymerase.

In one embodiment, lNTPs are incorporated into the newly-synthesized portion of the molecule by a polymerase capable of synthesizing LNA from a DNA template. The LNA region is then displaced from the template molecule resulting in a DNA-LNA fusion molecule. The resultant display library is a mLNAP library. Exemplary polymerases capable of synthesizing LNA from a DNA template that can be used in the methods of the invention include, but are not limited to, polC7 and polD4K polymerase.

In one embodiment, aNTPs are incorporated into the newly-synthesized portion of the molecule by a polymerase capable of synthesizing ANA from a DNA template. The ANA region is then displaced from the template molecule resulting in a DNA-ANA fusion molecule. The resultant display library is a mANAP library. Exemplary polymerases capable of synthesizing ANA from a DNA template that can be used in the methods of the invention include, but are not limited to, polC7 and polD4K polymerase.

In one embodiment, phNTPs are incorporated into the newly-synthesized portion of the molecule by a polymerase capable of synthesizing phNA from a DNA template. The phNA region is then displaced from the template molecule resulting in a DNA-phNA fusion molecule. The resultant display library is a mphNAP library. Exemplary polymerases capable of synthesizing phNA from a DNA template that can be used in the methods of the invention include, but are not limited to, PGV2 polymerase.

In one embodiment, faNTPs are incorporated into the newly-synthesized portion of the molecule by a polymerase capable of synthesizing FANA region is then displaced from the template molecule resulting in a DNA-FANA fusion molecule. The resultant display library is a mFANAP library. Exemplary polymerases capable of synthesizing FANA from a DNA template that can be used in the methods of the invention include, but are not limited to, D4K enzyme, 9oN DNA polymerase, Tgo DNA polymerase, Kod DNA polymerase and Deep vent DNA polymerase.

In one aspect, described herein are mXNAP display libraries displaying TNA, HNA, CeNA, LNA, ANA, pHNA or FANA aptamers, or combinations thereof. In certain embodiments, the mXNAP display library comprises molecules for the display of at least $10^5$, $10^6$, $10^7$, $10^8$, $10^9$, $10^{10}$, $10^{11}$, $10^{12}$, $10^{13}$, or at least $10^{14}$ different XNA aptamers.

In one aspect, provided herein is a method of preparing a XNA particle display library comprising the steps of: (a) providing a population of monoclonal particles, wherein each particle comprises a plurality of self-priming, stem-loop forming, template DNA molecules, each of which comprises a stem-loop forming priming sequence, a DNA coding region and a fixed sequence primer binding site; (b) extending the primer in the presence of an XNA polymerase and one or more XNA triphosphate molecules (xNTPs) to form a population of double stranded XNA-DNA hybrid particles; and (c) contacting the double stranded XNA-DNA hybrid particles with a primer which anneals to the loop region of the stem-loop structure and extending the DNA primer using dNTPs and a DNA polymerase to displace the XNA portion of the XNA-DNA display templates to form a population of display particles comprising plurality dsDNA-ssXNA fusion display molecules.

Screening Methods

In one aspect, provided herein is a method of screening for XNA aptamers having a desired property comprising: (i) incubating a mXNAP display library containing XNA aptamers with at least one candidate interaction partner for an amount of time sufficient for interaction (e.g., binding) of the XNA aptamers with the candidate interaction partner; (ii) washing to remove the unbound XNA aptamers; (iii) selecting XNA aptamers that have the desired property.

The desired property may be a target binding activity or a target-binding induced activity, e.g., a catalytic activity or a modified catalytic activity; inhibition activity, activation activity, or a modification of an inhibition activity or activation activity; structure switching activity or a modification of a structure switching activity; or cooperative activity. In some embodiments, the desired property is a target binding activity or a target-binding induced activity. In some embodiments, the target binding activity is one of affinity, specificity and bi-specificity.

In one such embodiment, the target binding activity is specificity, and the screening method includes a step of exposing the plurality of mXNAP to a first target and a second target. Nucleic acid agents having the desired property will exhibit a specific binding affinity (e.g, a Kd of from about 1 pM to about 100 nM, e.g., a Kd of from about 1 pM to about 10 nM, or a Kd of from about 1 pM to about 5 nM) for either the first target or the second target but not both. For example, the first target may be a first homolog or splicing variant of a protein and the second target may be a second homolog or splicing variant of the protein. In another embodiment, the first target may be a first post-translational modification form of a protein and the second target may be a second post-translation modification form of a protein. In another embodiment, the first target may be a protein which has been subjected to a post-translational modification and the second target may be a form of the protein which has not been subjected to the post-translational modification. For example, a nucleic acid agent having the desired property may bind to a phosphorylated form of a protein but not the unphosphorylated form or vice versa.

A variety of post-translational modifications are known in the art, e.g., myristoylation, palmitoylation, isoprenylation or prenylation, glypiation, lipoylation, the addition of flavin, the addition of heme C, phosphopantetheinylation, retinylidene Schiff base formation, acylation (e.g., acetylation), alkylation (e.g., methylation), amide bond formation, glycosylation, nucleotide addition, oxidation, phosphate ester (O-linked) or phosphoramidate (N-linked) formation (e.g., phosphorylation and adenylylation), glycation, biotinylation and PEGylation, among others.

In some embodiments, the first target is a first conformational form of a protein and the second target is a second conformational form of the protein. For example, the first target may be a ligand-bound form of an enzyme and the second target may be an unbound form of the same enzyme or vice versa.

In some embodiments, the target binding activity is bi-specificity. In such embodiments, the screening method may include a step of exposing the plurality of display molecules to a first target and a second target. Nucleic acid agents having the desired property will exhibit a specific binding affinity (e.g, a Kd of from about 1 pM to about 100 nM, e.g., a Kd of from about 1 pM to about 10 nM, or a Kd of from about 1 pM to about 5 nM) for both the first and second target. In such embodiments, the first target may be a first homolog or splicing variant of a protein and the second target may be a second homolog or splicing variant of the protein. The first target may be a first post-translational modification form of a protein and the second target may be a second post-translation modification form of a protein, e.g., as described above. In addition, the first target may be a protein which has been subjected to a post-translational modification and the second target may be a form of the protein which has not been subjected to the post-translational modification, e.g., as described above. The first target may be a first conformational form of a protein and the second target may be a second conformational form of the protein, e.g., as described above.

In some embodiments, multiple detectable labels may be used to facilitate the screening process. For example, where the target binding activity is specificity, the screening method may include exposing the plurality of display molecules to a first target labeled with a first detectable label and a second target labeled with a second detectable label, wherein the first detectable label and the second detectable label are different. Nucleic acid agents having the desired property will exhibit a first binding affinity for the first target and a second binding affinity for the second target, wherein the first binding affinity and the second binding affinity are significantly different. These binding affinities may be determined via detection of the detectable labels. For example, in order to screen for aptamers that specifically bind to a thrombin protein in serum, thrombin can be labeled with a first detectable label while all other serum proteins are labeled with a second, different detectable label. Aptamers associated with a relatively high signal from the first detectable label, which is indicative of relatively high affinity thrombin binding, and a relatively low signal from the second detectable label, which is indicative of relatively low affinity binding to other serum proteins, may be selected.

Similarly, multiple detectable labels may be used where the target binding activity is bi-specificity. For example, the screening method may include exposing the plurality of display molecules to a first target labeled with a first detectable label and a second target labeled with a second detectable label, wherein the first detectable label and the second detectable label are different. Nucleic acid agents having the desired property will exhibit a specific binding affinity (e.g, a Kd of from about 1 pM to about 100 nM, e.g., a Kd of from about 1 pM to about 10 nM, or a Kd of from about 1 pM to about 5 nM) for both the first and second target, which binding affinity may be determined via detection of the detectable labels.

Isolation and/or sorting as described herein may be conducted using a variety of methods and/or devices known in the art, e.g., flow cytometry (e.g., Fluorescence Activated Cell Sorting (FACS) or Ramen flow cytometry), fluorescence microscopy, optical tweezers, micro-pipettes, and microfluidic magnetic separation devices and methods. In some embodiments, where the detectably labeled target is a fluorescently labeled target, Fluorescence Activated Cell Sorting (FACS) may be utilized to quantitatively sort particle immobilized candidate nucleic acid agents or aptamer particles based on one or more fluorescence signals. One or more sort gates or threshold levels may be utilized in connection with one or more detectable labels to provide quantitative sorting over a wide range of candidate nucleic acid agent-target interactions or candidate aptamer sequence-target interactions. In addition, the screening stringency may be quantitatively controlled, e.g., by modulating the target concentration and setting the position of the sort gates.

Where, for example, the fluorescence signal is related to the binding affinity of the candidate nucleic acid agents or candidate aptamer sequences for the target, the sort gates and/or stringency conditions may be adjusted to select for nucleic acid agents or aptamers having a desired affinity or desired affinity range for the target. In some cases, it may be desirable to isolate the highest affinity nucleic acid agents or aptamers from a particular library of candidate nucleic acid agents or candidate aptamer sequences. However, in other cases nucleic acid agents or aptamers falling within a particular range of binding affinities may be isolated.

Targets

Candidate nucleic acid agents and aptamers may be generated and screened as described herein to identify nucleic acid agents and aptamers which bind to a variety of targets, e.g., target molecules. Suitable targets may include, for example, small molecules (e.g., organic dyes, toxins, etc.), amino acids, carbohydrates, lipids, aminoglycosides, antibiotics, peptides, proteins, post-translational modifications, nucleic acids, liposomes, virus, whole cells, cellular components, tissues, living organisms, or an unknown target or mixture. Small molecule targets of interest generally have a molecular weight of about 1000 Daltons, e.g., less than 800 Daltons. Protein targets of interest may include, for example, cell surface receptors, signal transduction factors, and hormones. Cellular targets of interest may include, for example, mammalian cells, particularly human cells; stem cells; tumor cells and bacterial cells.

More than one type of target may be utilized simultaneously in the screening methods disclosed herein. For example, two or more protein targets having different amino acid sequences may be simultaneously screened against a single library of candidate nucleic acid agents or candidate aptamer sequences.

In some embodiments, a target molecule or a molecule associated with a target molecule, e.g., via a binding interaction, may be detectably labeled as described herein.

Labels

Suitable labels which may be used to provide a detectably labeled target or detectably labeled nucleic acid agent, e.g., aptamer, according to the present disclosure may include radioactive isotopes, fluorescers, chemiluminescers, chromophores, enzymes, enzyme substrates, enzyme cofactors, enzyme inhibitors, dyes, metal ions, metal sols, ligands (e.g., biotin, avidin, strepavidin or haptens), affinity tags and the like.

Exemplary affinity tags suitable for use include, but are not limited to, a monocytic adaptor protein (MONA) binding peptide, a T7 binding peptide, a streptavidin binding peptide, a polyhistidine tract, protein A (Nilsson et al., EMBO J. 4:1075 (1985); Nilsson et al., Methods Enzymol. 198:3 (1991)), glutathione S transferase (Smith and Johnson, Gene 67:31 (1988)), Glu-Glu affinity tag (Grussenmeyer et al., Proc. Natl. Acad. Sci. USA 82:7952 (1985)), substance P, FLAG peptide (Hopp et al., Biotechnology 6:1204 (1988)), or other antigenic epitope or binding domain. See, in general, Ford et al., Protein Expression and Purification 2:95 (1991). DNA molecules encoding affinity tags are available from commercial suppliers (e.g., Pharmacia Biotech, Piscataway, N.J.).

Any fluorescent polypeptide (also referred to herein as a fluorescent label) may be suitable for use as a detectable label. A suitable fluorescent polypeptide will be one that will readily provide a detectable signal that can be assessed qualitatively (positive/negative) and quantitatively (comparative degree of fluorescence). Exemplary fluorescent polypeptides include, but are not limited to, yellow fluorescent protein (YFP), cyan fluorescent protein (CFP), GFP, mRFP, RFP (tdimer2), HCRED, etc., or any mutant (e.g., fluorescent proteins modified to provide for enhanced fluorescence or a shifted emission spectrum), analog, or derivative thereof. Further suitable fluorescent polypeptides, as well as specific examples of those listed herein, are provided in the art and are well known.

Biotin-based labels also find use in the methods disclosed herein. Biotinylation of target molecules is well known, for example, a large number of biotinylation agents are known, including amine-reactive and thiol-reactive agents, for the biotinylation of proteins, nucleic acids, carbohydrates, carboxylic acids; see, e.g., chapter 4, Molecular Probes Catalog, Haugland, 6th Ed. 1996, hereby incorporated by reference. A biotinylated substrate can be detected by binding of a detectably labeled biotin binding partner, such as avidin or streptavidin. Similarly, a large number of haptenylation reagents are also known.

Pharmaceutical Compositions

In some embodiments, XNA aptamers identified according to the methods of the invention can function as pharmaceutical agents. For example, in one embodiment, HIV-RT 3.17 can be used as an anti-HIV agent for the treatment or prevention of HIV or an HIV associated disease or disorder.

Therefore, in one embodiment, the invention also relates to a pharmaceutical composition comprising a therapeutically effective amount of an XNA aptamer of the invention, optionally in combination with one or more other active ingredients and/or with a pharmaceutically acceptable carrier. Moreover, XNA aptamers of the invention may be used in a method for the treatment of a disease or disorder, comprising administering a therapeutically effective amount of the XNA aptamer of the invention to a subject in need thereof.

The pharmaceutical composition of the present invention comprises at least one XNA aptamer selected according to the methods of the invention. The compositions include those suitable for oral, topical, intravenous, subcutaneous, nasal, ocular, pulmonary, and rectal administration. The compounds of the invention can be administered to mammalian individuals, including humans, as therapeutic agents.

For example, the compounds of the invention are useful as antiviral agents. The present invention provides a method for the treatment of a patient afflicted with a viral infection comprising administering to the patient a therapeutically effective antiviral amount of a compound of the invention. The term "viral infection" as used herein refers to an abnormal state or condition characterized by viral transformation of cells, viral replication and proliferation. In one embodiment, the viral infection is an HIV infection and the XNA aptamer of the invention is HIV-RT 3.17.

A "therapeutically effective amount" of a compound of the invention refers to an amount which is effective, upon single or multiple dose administration to the patient, in controlling the growth of e.g., the microbe or tumor or in prolonging the survivability of the patient beyond that expected in the absence of such treatment. As used herein, "controlling the growth" refers to slowing, interrupting, arresting or stopping the microbial or proliferative transformation of cells or the replication and proliferation of the microbe and does not necessarily indicate a total elimination of e.g., the microbe or tumor.

Accordingly, the present invention includes pharmaceutical compositions comprising, as an active ingredient, at least one of the compounds of the invention in association with a pharmaceutical carrier. The compounds of this invention can be administered by oral, parenteral (intramuscular, intraperitoneal, intravenous (IV) or subcutaneous injection), topical, transdermal (either passively or using iontophoresis or electroporation), transmucosal (e.g., nasal, vaginal, rectal, or sublingual) or pulmonary (e.g., via dry powder inhalation) routes of administration or using bioerodible inserts and can be formulated in dosage forms appropriate for each route of administration.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating, agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

Topical formulations will generally comprise ointments, creams, lotions, gels or solutions. Ointments will contain a conventional ointment base selected from the four recognized classes: oleaginous bases; emulsifiable bases; emulsion bases; and water-soluble bases. Lotions are preparations to be applied to the skin or mucosal surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Creams, as known in the art, are viscous liquid or semisolid emulsions, either oil-in-water or water-in-oil. Topical formulations may also be in the form of a gel, i.e., a semisolid, suspension-type system, or in the form of a solution.

Formulations of these drugs in dry powder form for delivery by a dry powder inhaler offers yet another means of administration. This overcomes many of the disadvantages of the oral and intravenous routes.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired. Generally, dosage levels of between 0.001 to 10 mg/kg of body weight daily are administered to mammals.

Kits

The present invention also relates to a kit for performing any of the above described methods. In one embodiment, the kit comprises at least one reagent for use in a method of generating a mXNAP display library of the invention. In one embodiment, the kit may comprise a mixture of xNTPs and an XNA polymerase for the synthesis of a mXNAP display library of the invention. In one embodiment, the kit may comprise an mXNAP display library of the invention. In some embodiments, one or more of the components are premixed in the same reaction container. In particular embodiments, the kit additionally comprises instructional material.

In one embodiment, the kit comprises at least one XNA aptamer identified according to a method of the invention and instructions for use of the XNA aptamer. In one embodiment, the XNA aptamer is a TNA aptamer. In one embodiment, the XNA aptamer is HIV-RT 3.17.

EXPERIMENTAL EXAMPLES

The invention is further described in detail by reference to the following experimental examples. These examples are provided for purposes of illustration only, and are not intended to be limiting unless so specified. Thus, the invention should in no way be construed as being limited to the following examples, but rather, should be construed to encompass any and all variations which become evident as a result of the teaching provided herein. Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure Example 1 mXNAP Display

Figure 2:
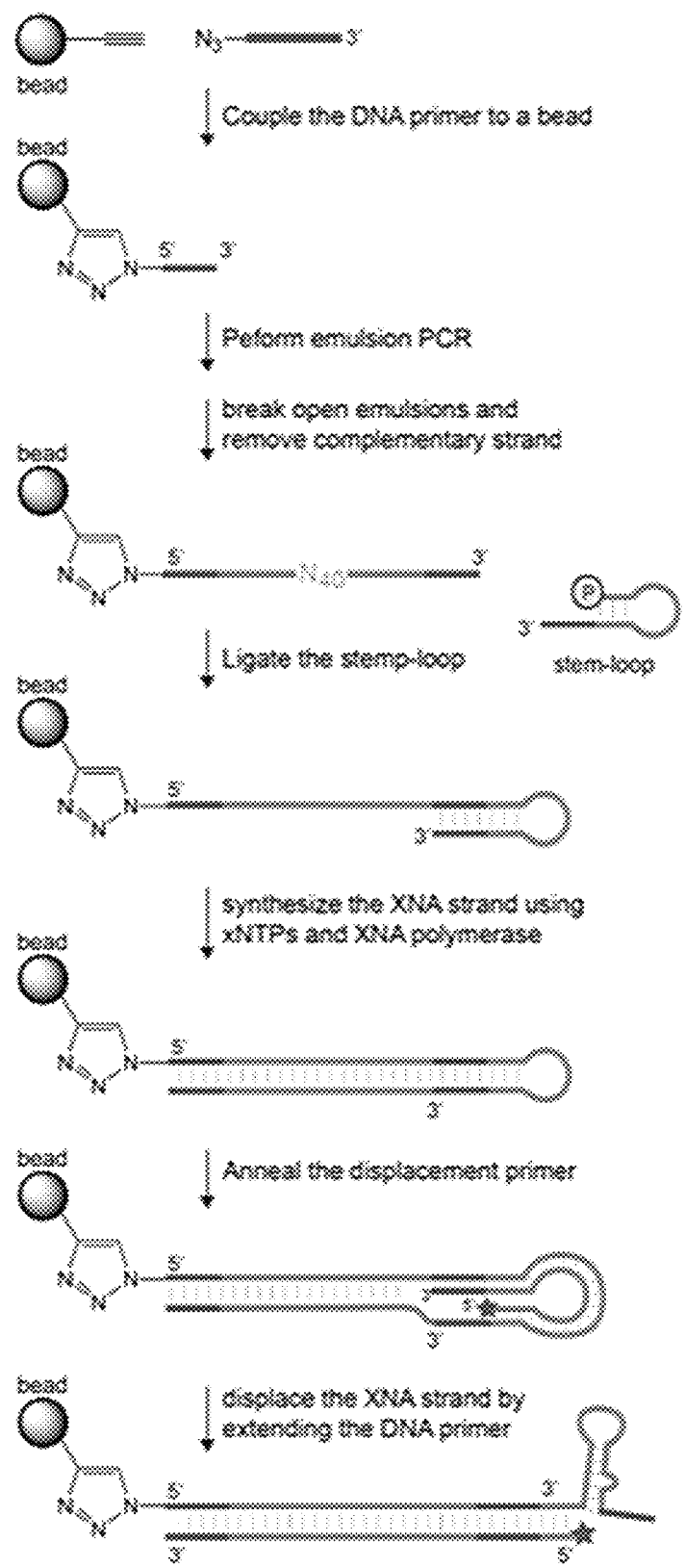
FIG. 2 depicts a schematic diagram of the generation of XNA particle display molecules.
Figure 3:
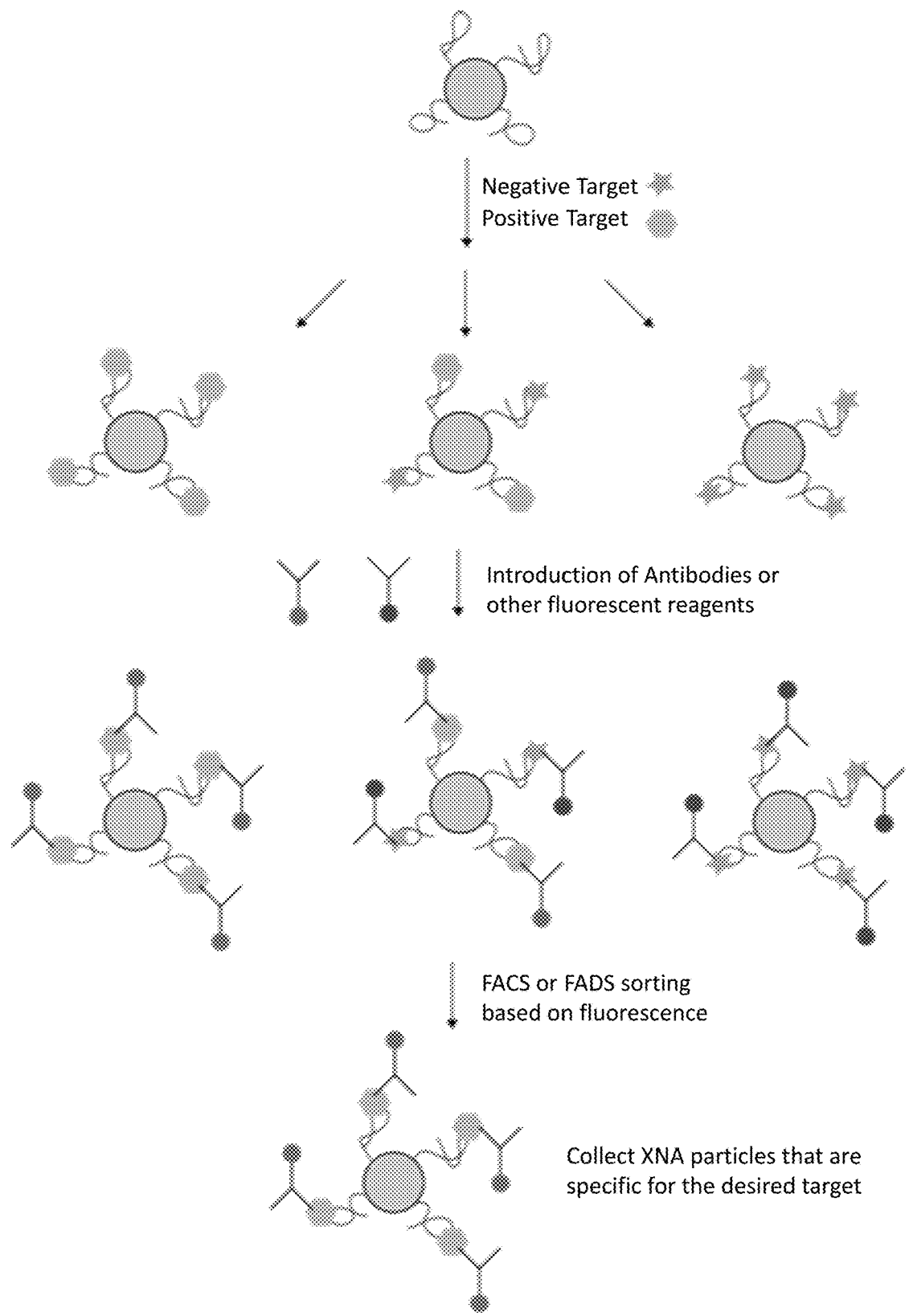
FIG. 3 depicts a schematic diagram of a screening method for detecting a target protein using the XNA particle display molecules.

A method of displaying XNA aptamers as a particle display library has been developed. This method uses a modified version of DNA display, which is a strategy for covalently linking newly synthesized XNA strands to their encoding double-stranded DNA, to allow construction of XNA aptamer particles. Schematic diagrams detailing the strategy are provided in FIG. 1 through FIG. 3. For the generation of an XNA particle display library, a fixed primer sequence is coupled to a bead. Monoclonal beads are then generated to have a single unique template DNA sequence encoding an XNA aptamer using emulsion PCR. The emulsion is then broken and the and complementary strands are removed prior to ligation of a self-priming stem-loop forming DNA molecule to the particle-bound template DNA sequence. Synthesis by a XNA polymerase from the self-priming end of the stem-loop forming DNA molecule then incorporates xNTPs to form a DNA-XNA hybrid molecule. Strand displacement of the XNA aptamer using a primer that binds to the stem-loop forming molecule then generates monoclonal particle bound dsDNA-XNA display molecules.

Example 2

Generating Biologically Stable TNA Aptamers that Function with High Affinity and Thermal Stability Although antibodies remain the gold standard for protein affinity reagents, they also represent the greatest source of problems in biomedical research (Baker et al., 2015, Nature 521:274-276). The sensitivity of antibodies to elevated temperatures demonstrates a critical weakness that limits their shelf-life, reproducibility, and performance in functional assays. Thermal instability could be linked to problems with batch-to-batch variability that have plagued antibody research. In one striking example, the results from only six of 53 high profile cancer research papers could be reproduced (Begley and Ellis, 2012, 2012, Nature 483:531-533). In another study, 25% of 246 antibodies used for epigenetic research failed tests for specificity (Egelhofer et al., 2011, Nat. Struct. Mol. Biol. 18, 91-93). Similarly, 49 antibodies generated against 19 signaling proteins had bound to more than one target, meaning that their results could not be trusted 34. Given these problems, researchers are calling for better standardization methods and access to new types of affinity reagents (Bradbury and Pluckthun, 2015, Nature, 518:27-29; Marx et al., 2013, Nat. Methods 10:29-833).

The experiments presented herein outline a selection approach for evolving biologically stable aptamers based on the framework of α-L-threofuranosyl nucleic acid (TNA, FIG. 4A) (Schöning et al., 2000, Science, 290:1347-1351) an artificial genetic system discovered by Eschenmoser and colleagues as part of a systematic investigation into the chemical etiology of RNA (Eschenmoser, 1999, Science, 284:2118-2124). Despite a backbone repeat unit that is one atom (or bond) shorter than its natural counterpart, TNA is capable of efficient Watson-Crick base pairing with itself and with complementary strands of DNA and RNA (Schöning et al., 2000, Science, 290:1347-1351; Yang et al., 2007, J. Mol. Evol. 65:289-295). More recently, biological studies have shown that TNA is completely refractory to nuclease digestion, making it a promising candidate for biological applications that require target-specific binding in environments where natural genetic polymers rapidly degrade (Culbertson et al., 2016, Bioorg. Med. Chem. Lett. 26:2418-2421). The strategy taken is analogous to protein display technologies, such as mRNA display, that provide a covalent link between the encoding messenger RNA template (genotype) and translated protein (phenotype) (Roberts and Szostak, 1997, Proc. Natl. Acad. Sci. USA 94:12297-12302). However, in this case, freshly synthesized TNA is physically linked to its complementary DNA template, which is present in double-stranded (ds) form (FIG. 4B) (Ichida et al., 2005, J. Am. Chem. Soc. 127:2802-2803). In this configuration, TNA molecules isolated from the selection are amplified by PCR using the dsDNA portion of the molecule as the template for the polymerase. This approach is sufficiently general that it could be applied to any XNA polymer (artificial genetic polymers with non-ribose sugars) for which a polymerase is available to copy DNA templates into XNA (Chaput et al., 2012, Chem. Biol. 19, 1360-1371). It also avoids the need for an XNA reverse transcriptase, which are difficult to generate by polymerase engineering and tend to function with weak template binding affinity. The latter problem is particularly acute, as it can limit the recovery of functional sequences when small numbers of XNA molecules are present after stringent washing steps have been carried out to remove weaker affinity sequences.

Although substantially more work is needed, including access to building blocks with greater chemical diversity, the data suggests that alternative protein affinity reagents, like TNA aptamers, may offer certain advantages to antibodies. Unlike most aptamers, TNA is completely recalcitrant to nuclease digestion and is amenable to in vitro selection against any biological protein of therapeutic or diagnostic interest. The latter provides an important benefit over Spiegelmers, whose targets must be generated by chemical synthesis. Relative to antibodies, TNA is capable of achieving KDs with picomolar binding while also avoiding unwanted problems associated with thermal denaturation. The ability to fold cooperatively into functional structures, combined with their chemical synthesis, solves the cold-chain problem and could improve the reproducibility and performance of protein affinity reagents.

The results presented herein establish that TNA aptamers have the ability to function with high biological stability, protein binding affinity, and thermal stability. These data offer a possible solution to the antibody problem and provide strong support for the continued development of TNA reagents for diagnostic and therapeutic applications. Such projects open the door to a new generation of affinity reagents that could one day overcome some of the weaknesses of existing technologies.

The results of the experiments are now described.

The selection (FIG. 4B) was performed by extending a self-priming DNA library with chemically synthesized TNA triphosphates (tNTPs) (Sau et al., 2016, J. Org. Chem. 81:2302-2307; Sau and Chaput, 2017, Org. Lett. 19:4379-4382) using an engineered TNA polymerase that was previously developed to synthesize TNA on DNA templates (Larsen et al., 2016, Nat. Commun. 7:11235; Chim et al., 2017, Nat Commun 8:1810). The product of the primer-extension step is a chimeric TNA-DNA hairpin duplex in which a 40 nt random region and downstream fixed-sequence primer binding site are successfully copied into TNA. The TNA portion of the duplex was displaced in a separate step by extending a DNA primer annealed to the loop region of the hairpin with DNA, which results in a combinatorial library of single-stranded TNA molecules that are each physically linked to their encoding dsDNA templates. To enrich for TNA molecules with affinity to a specific target, the pool of TNA-dsDNA fusion molecules was incubated with a protein target, and bound sequences are recovered and amplified by PCR. A second PCR step was performed with a PEG-modified DNA primer and the single-stranded, PEGylated DNA template was obtained after purification by denaturing polyacrylamide gel electrophoresis (PAGE). The template strand was then ligated to the DNA stem-loop structure, extended with TNA, and strand displaced to reconstruct the TNA library for another round of in vitro selection.

The DNA display approach was applied to select TNA aptamers with affinity to a recombinant reverse transcriptase (RT) isolated from the human immunodeficiency virus (HIV). HIV RT is the replicative polymerase for HIV and thus a major target for drug development (Bala et al., 2018, RNA Biol 15:327-337). Although previous selections have generated DNA and FANA (2'-fluoroarabino nucleic acid) aptamers to HIV RT (Michalowski et al., 2008, Nucleic Acids Res. 36:7124-7135; Alves Ferreira-Bravo, 2015, Nucleic Acids Res. 43:9587-9599), both classes of affinity reagents are susceptible to nuclease digestion (Watts et al., 2009, Org Biomol Chem 7:1904-1910). These studies were extended by establishing a biologically stable aptamer to this target that could function with high binding affinity under harsh biological conditions, without the need for extensive chemical modifications that have been previously used to improve the biological stability of DNA aptamers (Eaton et al., 1997, Bioorg. Med. Chem. 5:1087-1096). A key question to address was whether TNA could fold into structures with the same level of high affinity binding (picomolar $K_D$ values) commonly observed for high quality monoclonal antibodies (mAbs). Although a TNA aptamer that binds to HIV RT with a $K_D$ of ~5 nM was previously isolated, that example utilized a reverse transcription step and required next-generation sequencing data to identify an aptamer with higher affinity binding (Mei et al., 2018, J. Am. Chem. Soc. 140:5706-5713). Recognizing that the current TNA reverse transcriptase functions with weak activity (Dunn and Chaput, 2016, ChemBioChem 17:1804-1808), without being bound by theory, it was reasoned that a DNA display approach should make it possible to recover high affinity sequences that may have been lost in the previous selection due to the inherent limitations of the current TNA reverse transcriptase (Mei et al., 2018, J. Am. Chem. Soc. 140:5706-5713).

Figures 4A, 4B, 4C:
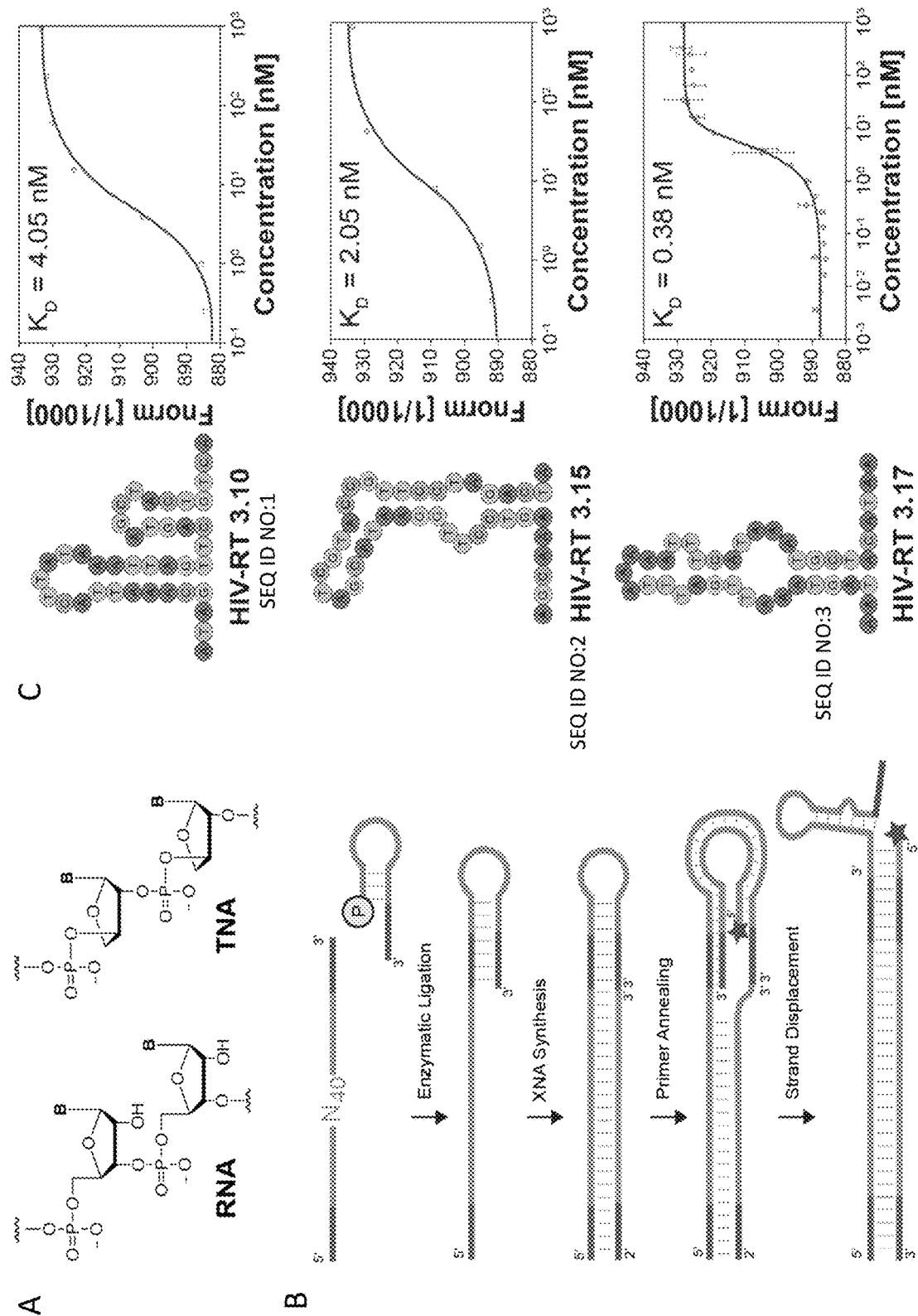
FIG. 4A through FIG. 4C depict the selection of High Affinity TNA Aptamers.

Three rounds of selection were performed starting from a population of $10^{13}$ different TNA molecules, each displayed on their encoding dsDNA. For each round of selection, the library was incubated with HIV RT, which was immobilized on the surface of a functionalized and passivated well of an amino modified-ELISA plate. After a 1-hour incubation (25° C.), the well was drained, unbound sequences were removed by washing with buffer, and non-specific interactions were disrupted through additional washing steps with a high ionic strength buffer. High affinity aptamers that remained bound to the target were then recovered by denaturing the complex at 70° C. with buffer containing 3.4 M urea. After three rounds of selective amplification, a portion of the pool was cloned into E. coli and 20 library members were submitted for Sanger sequencing. From this set, 15 high quality reads were obtained with no significant sequence similarity. Nine randomly selected clones were experimentally synthesized by primer-extension and their dissociation constants ($K_D$) were determined under equilibrium conditions by microscale thermophoresis (MST). The screen for protein binding activity resulted in $K_D$ values ranging from 400 pM to 70 nM with six of the nine sequences having $K_D$ values of <10 nM. The three highest affinity TNA aptamers (HIV-RT 3.10, HIV-RT 3.15, and HIV-RT 3.17) bound to HIV RT with $K_D$s of 4 nM, 2 nM, and 380 pM, respectively (FIG. 4C). The highest affinity aptamer, HIV-RT 3.17 ($K_D$ 380±115 pM), was evaluated in triplicate to ensure the reproducibility of our measurements.

Figures 5A, 5B, 5C, 5D:
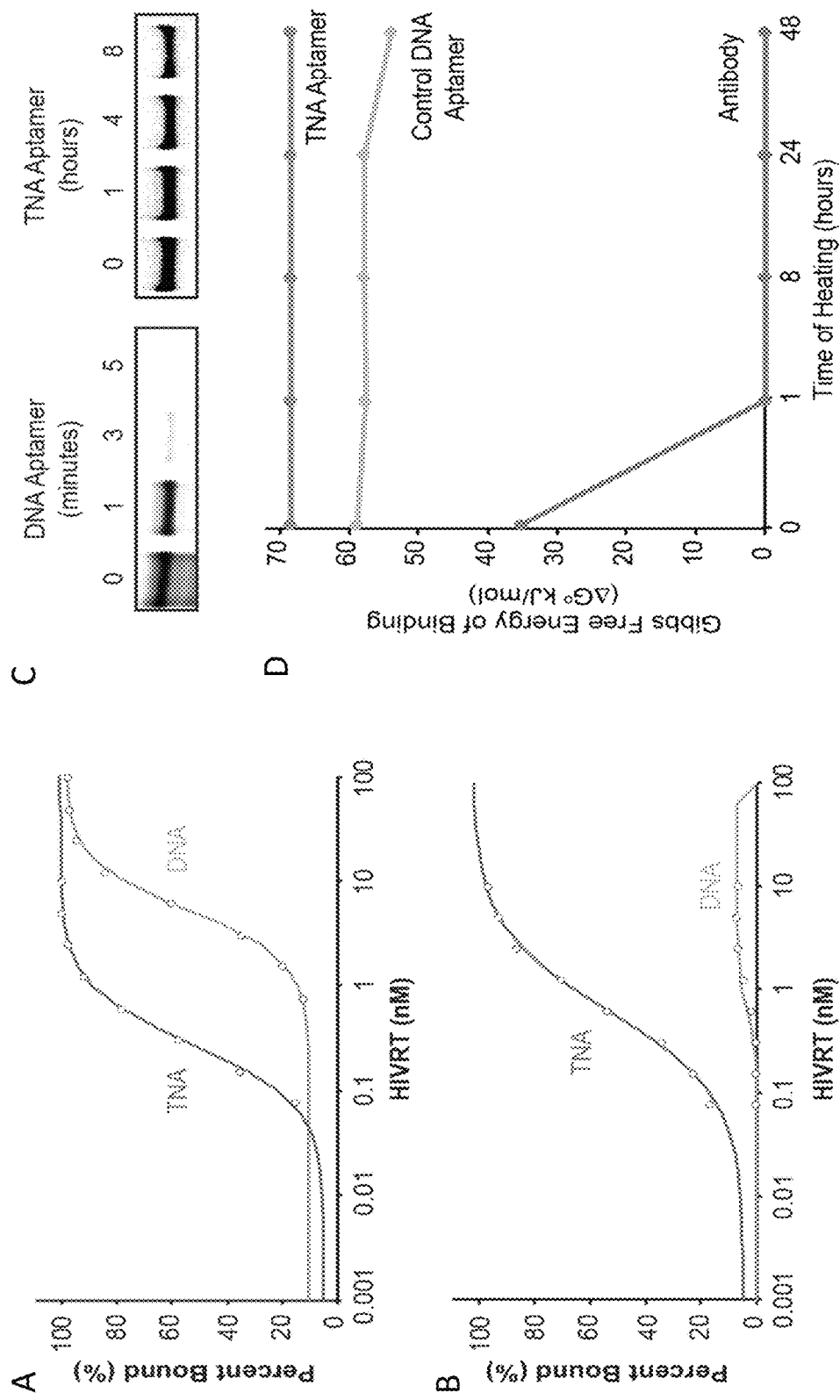
FIG. 5A through FIG. 5D, depicts the characterization of HIV-RT Aptamer 3.17.

To validate the affinity of HIV-RT 3.17, a second analytical technique was used to measure the $K_D$ of the aptamer to HIV RT. In this case, an electrophoretic mobility shift assay (EMSA) was used to evaluate the binding interaction by incubating the protein with a low concentration of labeled aptamer and varying the concentration of the protein target (FIG. 5A). As a positive control, the $K_D$ of R1T, a known DNA aptamer previously selected by Burke and colleagues to bind HIV RT (Michalowski et al., 2008, Nucleic Acids Res. 36:7124-7135), was measured. The resulting isotherms reveal that HIV-RT 3.17 binds to HIV RT with a $K_D$ of 196±86 pM and R1T binds with a $K_D$ of 4.5±0.41 nM. These values closely agree with the MST derived value of 380 pM for HIV-RT 3.17 and the literature $K_D$ for R1T (14±2 nM).

Next, the binding properties of HIV-RT 3.17 were evaluated under conditions where DNA aptamers and monoclonal antibodies are known to lose their activity. Since most aptamers are susceptible to nuclease digestion, the HIV RT binding assay was performed in the presence of snake venom phosphodiesterase (SVPE), a highly active 3' exonuclease that is used to degrade DNA and RNA into mononucleotides (Bowman et al., 2001, Nucleic Acids Res. 29: E101). In this assay, the HIV-RT 3.17 and R1T aptamers were incubated with SVPE for 1 hour at 37° C. prior to performing the equilibrium binding assay by EMSA. Analysis of the resulting binding curves revealed that HIV-RT 3.17 remains active in the presence of SVPE ($K_D$ of ~500 pM), while DNA digestion abrogates all protein-binding activity for the R1T aptamer (FIG. 5D). Time-dependent analysis of R1T digestion by denaturing PAGE reveals that the DNA aptamer degrades in minutes, while the TNA aptamer remains undigested after 24 hours of incubation at 37° C. (FIG. 5C).

Recognizing that antibodies are prone to rapid and irreversible unfolding at ambient temperature, a thermal challenge was performed by heating HIV-RT 3.17, R1T, and a commercial monoclonal antibody generated against HIV RT in buffer at 70° C. At designated time points between 0 and 48 hours, the reagents were cooled to room temperature and assayed for binding to HIV RT by biolayer interferometry (BLI). The $K_D$s from this data were used to calculate changes in the Gibbs free energy at standard conditions ($\Delta G°$), which were plotted as a function of temperature to illustrate the effect of heating on the affinity reagents (FIG. 5D). Visualizing these data in terms of binding energy as opposed to affinity affords a more intuitive picture of the effect of heating on the function of each binder. The results indicate that HIV-RT 3.17 and R1T retain full activity after 48 hours of heating at 70° C., while the monoclonal antibody lost activity within the first hour of heating. After 72 hours, the activities of both aptamers are reduced to 50%, presumably due to problems associated with thermal degradation.

To gain further insight into the function of HIV-RT 3.17, a secondary structure prediction calculation was performed using mFold (Zuker, 2003, Nucleic Acids Res. 31:3406-3415). Although mFold was developed to predict the secondary structure of DNA and RNA oligonucleotides, the algorithm favors the formation of Watson-Crick base pairs, making it a reasonable model for unnatural genetic polymers with phosphodiester backbones. HIV-RT 3.17 was predicted to adopt a step loop structure that contains two bulges (one large and one small) in the stem region (FIG. 4C). It also contains a predicted T:G wobble base pair and flanking sequences on both the 5' and 3' sides of the primary stem loop structure. Detailed structure-activity relationship studies confirmed the importance of both the stem loop structure and the wobble base pair for the bind to HIV RT. In general, deletions made throughout the primary stem loop structure of the HIV-RT 3.17 molecule reduced the binding activity by 2-10-fold. However, more significant drops in activity (17-100-fold) were observed when changes were made to the five base pairs that define the stem near the 5' and 3' termini. Even the mutation of a T:G wobble pair to a standard Watson-Crick C:G base resulted in a 10-fold loss in activity. Deletion of either the two 5' flanking nucleotides or the five 3' flanking nucleotides resulted in a ~3-fold reduction in binding affinity.

Figure 6:
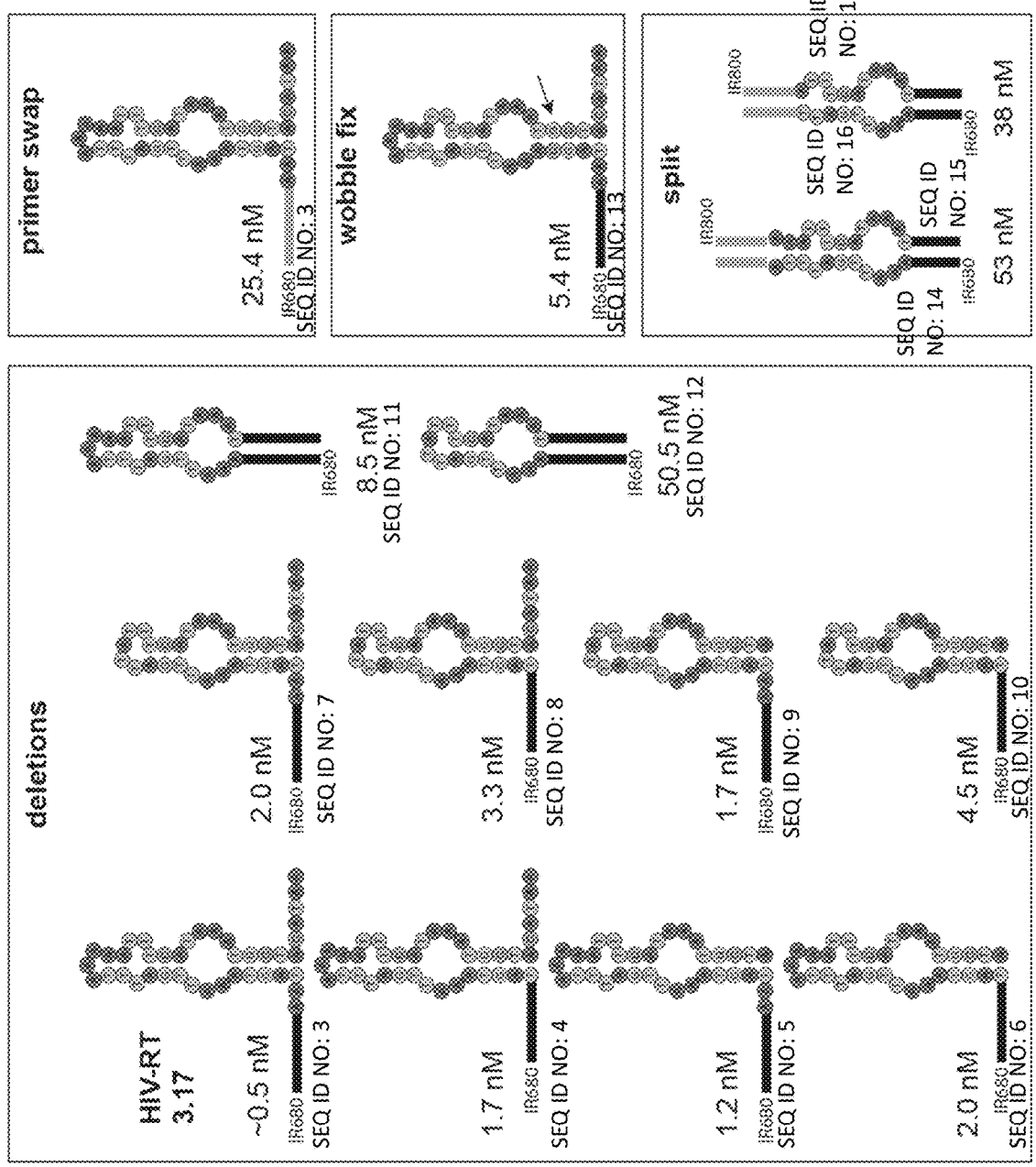
FIG. 6 depicts the structure activity relationship of HIV-RT aptamer 3.17. MST derived KD values characterizing the binding of HIV-RT aptamer 3.17 with deletions and mutations made to defined positions in the molecule.

Confident that HIV-RT 3.17 adopts a stem-loop structure, two split-aptamers were designed that function with $K_D$s of 40-50 nM (FIG. 6). The split-aptamer design is a common approach for biological sensors and has not previously been demonstrated for XNA polymers. Interestingly, replacing the five base pair stem in the primary stem-loop structure in both the unsplit and split aptamers resulted in a similar reduction in binding affinity. This suggests that the precise stem structure selected for in HIV-RT 3.17 likely provides more than structural integrity and may manifest in a more complex level of interaction with its protein target. More engineering of the split aptamer system based on the HIV1-RT structure may yield a split aptamer system with low nanomolar to picomolar affinity.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A method of screening for an XNA aptamer having a desired property, comprising the steps of:
  (a) obtaining a monoclonal xeno-nucleic acid aptamer particle (mXNAP) display library, comprising at least $10^5$ mXNAP display particles comprising a plurality of nucleic acid molecules comprising a dsDNA region and a single-stranded xeno-nucleic acid (XNA) aptamer region, wherein the mXNAP library is selected from the group consisting of a monoclonal threose nucleic acid aptamer particle (mTNAP), monoclonal hexitol nucleic acid aptamer particle (mHNAP), monoclonal cyclohexene nucleic acid aptamer particle (mCeNAP), monoclonal locked nucleic acid aptamer particle (mLNAP), monoclonal arabino nucleic acid aptamer particle (mANAP), monoclonal alkyl phosphonate nucleic acid aptamer particle (mphNAP), and monoclonal 2'-deoxy-2'-fluoroarabinonucleic acid aptamer particle (mFANAP) library,
  (b) incubating a mXNAP display library with at least one candidate interaction partner for an amount of time sufficient for interaction of the XNA aptamer regions with the candidate interaction partner; and (c) selecting mXNAP particles displaying XNA aptamers that have the desired property.

2. The method of claim 1, wherein the desired property is selected from the group consisting of a target binding activity and a target-binding induced activity.

3. The method of claim 2, wherein the target binding activity is selected from the group consisting of increased target affinity, increased target specificity and bi-specificity.

4. The method of claim 2, wherein the target-binding induced activity is selected from the group consisting of a catalytic activity, an inhibition activity, an activation activity, a switching activity and a cooperative activity.

5. The method of claim 2, wherein the target-binding induced activity is a modification of an activity selected from the group consisting of a catalytic activity, an inhibition activity, an activation activity, a switching activity and a cooperative activity.

* * * * *